(12) United States Patent
Sasaki et al.

(10) Patent No.: US 7,752,058 B2
(45) Date of Patent: Jul. 6, 2010

(54) PORTABLE TERMINAL AND HEALTH MANAGEMENT METHOD AND SYSTEM USING PORTABLE TERMINAL

(75) Inventors: Toshiaki Sasaki, Kanagawa (JP); Sadayuki Sugama, Ibaraki (JP); Takayoshi Tsutsumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1342 days.

(21) Appl. No.: 09/993,663

(22) Filed: Nov. 27, 2001

(65) Prior Publication Data

US 2002/0065685 A1    May 30, 2002

(30) Foreign Application Priority Data

| Nov. 30, 2000 | (JP) | ............................. 2000-365337 |
| Nov. 30, 2000 | (JP) | ............................. 2000-365935 |
| Nov. 30, 2000 | (JP) | ............................. 2000-365936 |
| Nov. 30, 2000 | (JP) | ............................. 2000-365937 |
| Nov. 30, 2000 | (JP) | ............................. 2000-365938 |
| Nov. 30, 2000 | (JP) | ............................. 2000-365939 |

(51) Int. Cl.
    *G06F 19/00* (2006.01)
(52) U.S. Cl. ............................. 705/3; 705/2; 455/566; 455/404
(58) Field of Classification Search ......... 128/200–203; 455/566, 404; 705/3, 2
    See application file for complete search history.

(56) References Cited

U.S. PATENT DOCUMENTS

| 4,695,954 | A |   | 9/1987 | Rose et al. ................... 364/413 |
| 4,838,275 | A | * | 6/1989 | Lee ............................ 600/483 |

(Continued)

FOREIGN PATENT DOCUMENTS

CN    1192703    9/1998

(Continued)

OTHER PUBLICATIONS

Japanese Official Action dated Feb. 23, 2009 in Japanese Application No. 2000-365937.

(Continued)

*Primary Examiner*—Gerald J. O'Connor
*Assistant Examiner*—Lena Najarian
(74) *Attorney, Agent, or Firm*—Fitzpatrick, Cella, Harper & Scinto

(57) ABSTRACT

A portable terminal carried and owned by each user is provided with a display screen, a communication unit, a memory storing personal information about each user, and an input/output device such as an inhaler. A database that communicates with each portable terminal is provided with a personal information storage unit storing the personal information about each user carrying the portable terminal, a medical information storage unit storing information about a medical facility, a drugstore, a medicine, and the input/output device, and a communication unit for communicating with each portable terminal. In the database, the user of the portable terminal is identified by collating the part of the information transmitted from the communication unit with information stored in the personal information storage unit. When a specific signal is transmitted from the communication unit, communication is performed with a medical facility while information, of the information stored in the medicine information storage unit, which is necessary for the user is provided for the portable terminal as an emergency measure. This makes it possible to properly and quickly handle an emergency.

27 Claims, 10 Drawing Sheets

U.S. PATENT DOCUMENTS

| | | | | |
|---|---|---|---|---|
| 4,934,358 | A | | 6/1990 | Nilsson et al. ......... 128/200.23 |
| 5,363,842 | A | * | 11/1994 | Mishelevich et al. ... 128/200.14 |
| 5,408,443 | A | * | 4/1995 | Weinberger ................... 368/10 |
| 5,472,143 | A | | 12/1995 | Bartels et al. ................ 239/462 |
| 5,694,919 | A | | 12/1997 | Rubsamen et al. ..... 128/200.14 |
| 5,710,551 | A | | 1/1998 | Ridgeway .............. 340/870.09 |
| 5,819,070 | A | | 10/1998 | Sasaki ........................ 395/500 |
| 5,894,841 | A | * | 4/1999 | Voges .................... 128/203.12 |
| 6,101,478 | A | | 8/2000 | Brown ............................. 705/2 |
| 6,198,914 | B1 | * | 3/2001 | Saegusa ................... 455/404.2 |
| 6,406,426 | B1 | * | 6/2002 | Reuss et al. ................. 600/300 |
| 6,408,330 | B1 | * | 6/2002 | DeLaHuerga .......... 709/217 |
| 6,564,121 | B1 | * | 5/2003 | Wallace et al. .............. 700/231 |
| 6,606,989 | B1 | | 8/2003 | Brand et al. |
| 6,944,464 | B2 | * | 9/2005 | Muranaga ................ 455/456.1 |
| 2001/0039503 | A1 | * | 11/2001 | Chan et al. ...................... 705/2 |
| 2001/0051787 | A1 | * | 12/2001 | Haller et al. ................. 604/66 |
| 2002/0059030 | A1 | * | 5/2002 | Otworth et al. ............... 702/19 |
| 2003/0036683 | A1 | * | 2/2003 | Kehr et al. .................. 600/300 |
| 2005/0060198 | A1 | * | 3/2005 | Bayne ........................... 705/2 |

FOREIGN PATENT DOCUMENTS

| | | |
|---|---|---|
| EP | 0 251 520 | 1/1988 |
| JP | 63-502885 | 10/1988 |
| JP | 07-022747 | 4/1995 |
| JP | 08-089483 | 4/1996 |
| JP | 8-329374 | 12/1996 |
| JP | 8-511966 | 12/1996 |
| JP | 11-047641 | 2/1999 |
| JP | 11-070086 | 3/1999 |
| JP | 11-353324 | 12/1999 |
| JP | 2000-166881 | 6/2000 |
| JP | 2000-311220 | 11/2000 |
| WO | 93/12823 | 7/1993 |
| WO | WO 93/12823 * | 7/1993 |
| WO | 97/00704 | 1/1997 |
| WO | 98/52633 A1 | 11/1998 |
| WO | 00/03344 | 1/2000 |
| WO | WO 00/32088 | 6/2000 |
| WO | 00/54205 | 9/2000 |
| WO | 00/70529 | 11/2000 |

OTHER PUBLICATIONS

Japanese Office Action dated Oct. 26, 2009 in corresponding Japanese Application No. JP 2000-365337.

European Search Report dated Dec. 10, 2009 in corresponding European Patent Application No. 01309878.5.

Chinese Office Action dated Sep. 18, 2009 in corresponding Chinese Patent Application No. 200810005685.3 and English language translation thereof.

* cited by examiner

FIG. 2A

PERSONAL DATA

| BASIC DATA | IDENTIFICATION DATA | HEALTH INSURANCE | ELECTRONIC CLINICAL CHART | MEASUREMENT DATA | DESIGNATED MEDICAL FACILITY |
|---|---|---|---|---|---|
| ADDRESS<br>NAME<br>DATE OF BIRTH<br>CONTACT<br>OCCUPATION<br>PLACE OF EMPLOYMENT | ID<br>PERSONAL CODE NUMBER<br>PASSWORD<br>AUTHENTICATION DATA | NUMBER<br>TYPE<br>USAGE LOG | CONSULTATION RECORD<br>PRESCRIPTION<br>MEDICATION DATA<br>HOSPITALIZATION RECORD<br>CASE HISTORY<br>FAMILY CASE HISTORY | HEIGHT<br>WEIGHT<br>BLOOD TYPE<br>BLOOD PRESSURE<br>BLOOD GLUCOSE LEVEL<br>URINE PROTEIN | INHALER SETTINGS |

FIG. 2B

MEDICAL DATA

| MEDICAL FACILITY DATA | | | | |
|---|---|---|---|---|
| REGISTRATION No. | LOCATION | CONTACT | REGISTERED DOCTOR | FACILITIES |
| | | | | |
| | | | | |

| PHARMACEUTICAL COMPANY DATA | | | |
|---|---|---|---|
| REGISTRATION No. | LOCATION | CONTACT | MEDICINES HANDLED | SCALE |
| | | | | |

| DRUGSTORE DATA | | | | |
|---|---|---|---|---|
| REGISTRATION No. | LOCATION | CONTACT | MEDICINES HANDLED | PHARMACEUTIST |
| | | | | |

| MEDICINE DATA | | |
|---|---|---|
| MEDICINE NAME | EFFECTS | CAUTIONS |
| | | |

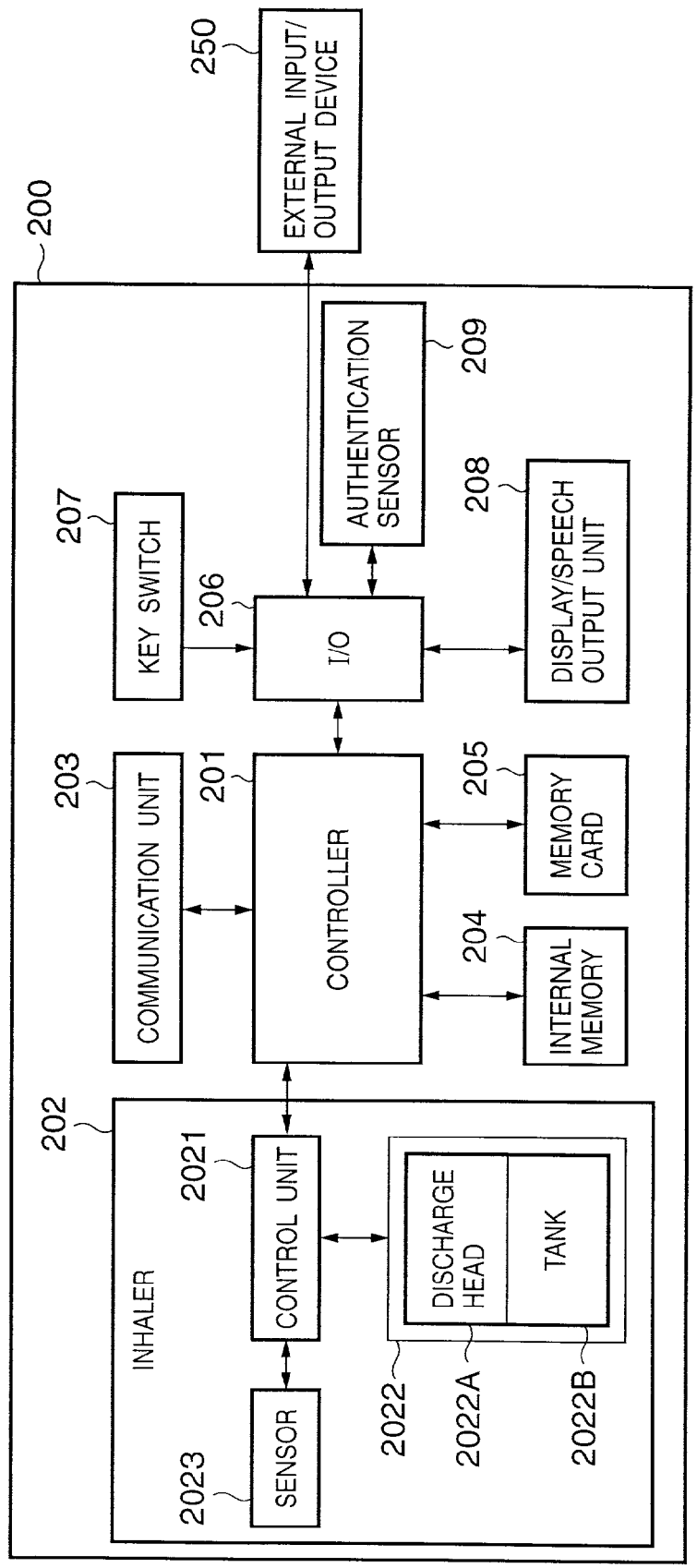

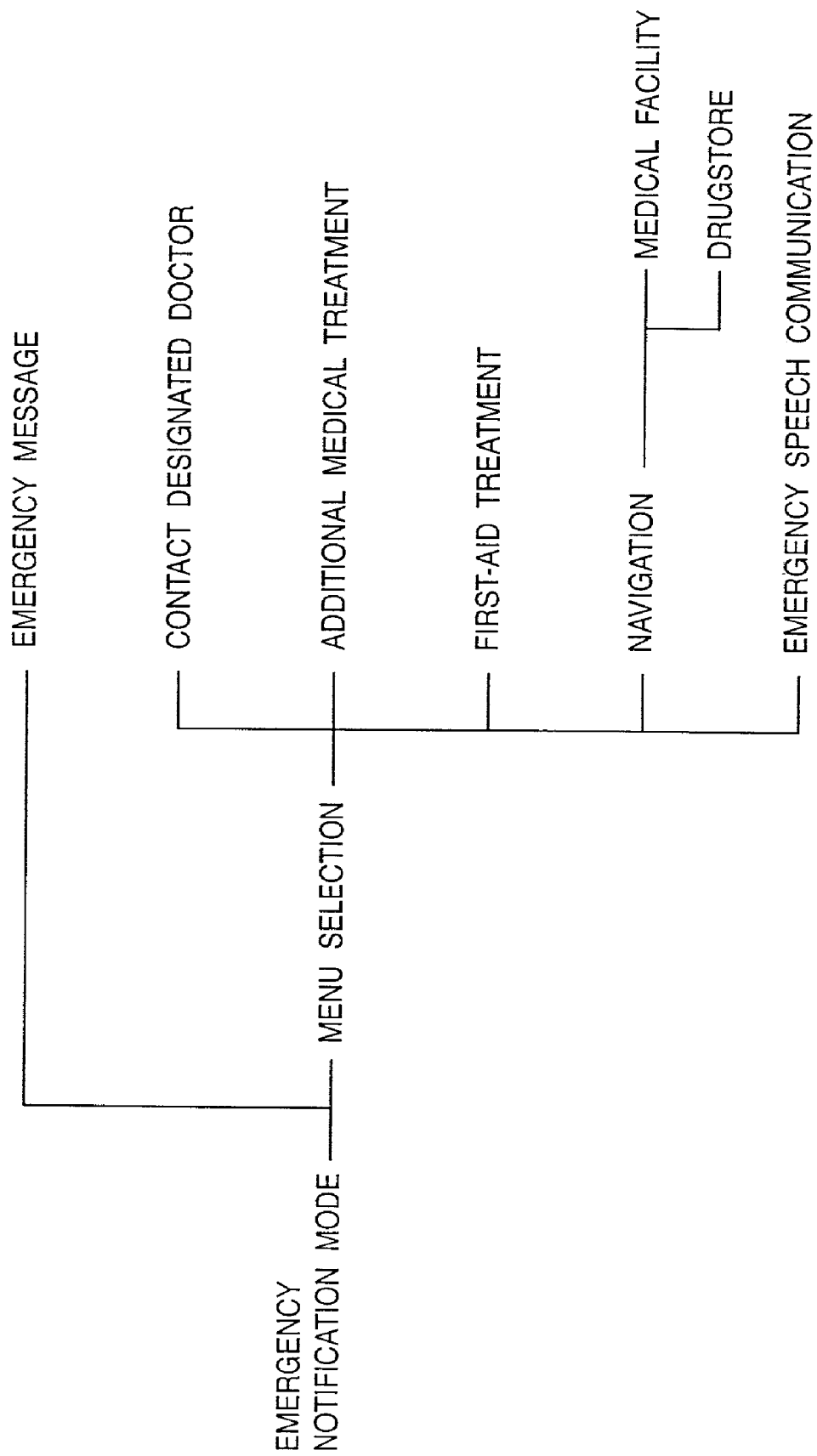

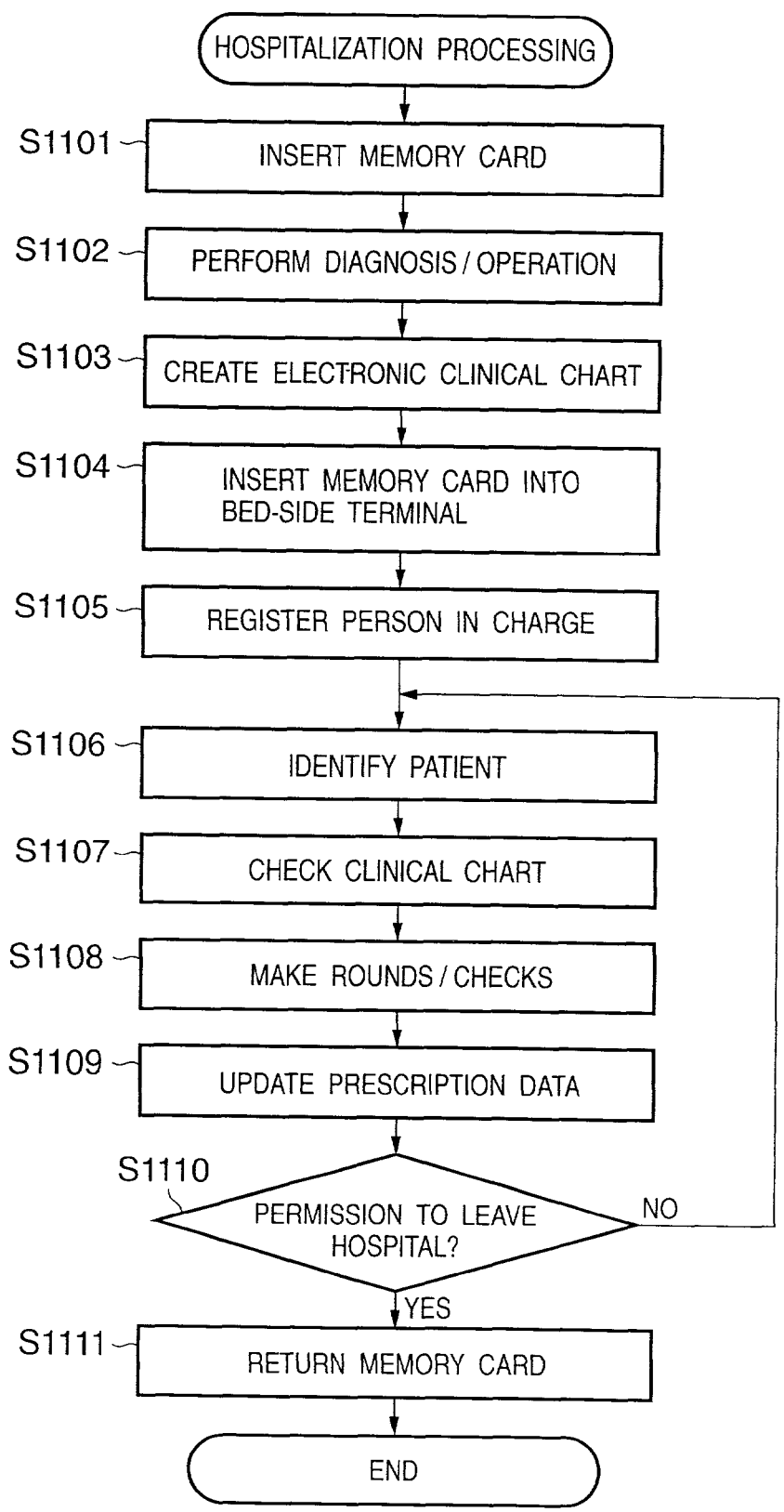

PORTABLE TERMINAL AND HEALTH MANAGEMENT METHOD AND SYSTEM USING PORTABLE TERMINAL

FIELD OF THE INVENTION

The present invention relates to a health management method and system using a portable terminal and, more particularly, to a method and system for managing personal information of a user by using a portable terminal having a radio communication function and an input/output device for supporting health management for the user.

The present invention also relates to a portable terminal having an inhaler and a method of controlling the inhaler and, more particularly, to a portable terminal having a portable terminal having a radio communication function and an input/output device for supporting health management for the user and a method of controlling the inhaler.

In addition, the present invention relates to a portable terminal having an inhaler and a method of controlling the inhaler and, more particularly, to a portable terminal having a storage means and an inhaler for discharging a medicine in the form of fine droplets and allowing a user to inhale the medicine and a method of driving the inhaler.

Furthermore, the present invention relates to a prescription determination assist method and system and, more particularly, to a prescription determination assist method and system for assisting in determining a prescription for a user carrying a memory card at a terminal installed in a medical facility.

Moreover, the present invention relates to an inhaler and a discharge head control method and, more particularly, to an inhaler for discharging a medicine in the form of fine droplets and allowing a user to inhale the medicine and a discharge head control method for the inhaler.

BACKGROUND OF THE INVENTION

With recent medical and scientific advances, the average life span of people is prolonged, and we are witnessing an aging society. On the other hand, owing to changes in eating habits and living environment, environmental contamination, viruses, and germs, new diseases and infections have been found. This has provoked anxiety among people about health. In so-called advanced nations, in particular, an increase in the number of people who suffer lifestyle-related illnesses such as diabetes and hyperpiesia raises a problem.

An increase in the number of medical facilities has not kept pace with an increase in the number of such patients. In addition, in some areas, there are no medical facilities that allow people to regularly visit. Under the circumstances, concerns are rising about future measures including policies against such situations.

Remote medical systems and home health management systems have therefore been proposed, which allow the aged and people suffering lifestyle-related diseases and chronic diseases to receive diagnoses from doctors and perform daily health management.

A typical arrangement of such systems is that a target individual installs a terminal at his/her home, and connects it to a server in a medical facility or center through a communication line such as the Internet so as to input/transmit answers for a medical inquiry and measurement values such as a blood pressure and bodily temperature from the terminal. A nurse or doctor then checks the data collected in the server and returns information indicating the presence/absence of an abnormality or message.

To manage such a medical system, clinical records (clinical charts) of users electronically recorded as electronic clinical charts and a medical database storing the data of the electronic clinical charts, various measurement values, and the like are required. Various proposals have been made about such electronic clinical charts and medical databases from various fields.

Electronic clinical charts, in particular, are effective in preventing medical malpractices and medication errors, which have become problems. A great deal of attention has been paid to an electronic clinical chart as a means for satisfying the patient's right to know by disclosing its contents to the patient or patient's family.

Terminals used in the above medical systems include a general personal computer having a display screen and input device and a dedicated terminal capable of measuring a specific value such as a blood pressure.

When a device such as a general personal computer is to be used as a terminal, settings for the device and its operation method become complicated. This limits people who can use such terminal.

Assume that dedicated terminals are used. In this case, if a user suffers a plurality of diseases or ailments and needs to perform various measurements, he/she must use a plurality of dedicated terminals. This is cumbersome operation and also increases burden on the user.

In a conventionally proposed medical system, if, for example, a user suffers a chronic disease or the like and needs to periodically take a medicine, the user must administer and manage a medicine by himself/herself, and there is no support function on the system side. For this reason, the burden of administration and management of medicines on users cannot be reduced.

More specifically, of diabetic patients who are currently on increase, patients suffering type I insulin-dependent diabetes mellitus must periodically take insulin because no insulin is secreted from the pancreas. Administration of insulin is currently performed by subcutaneous injection. This imposes great physical and mental burden on patients.

To reduce the burden on such patients, a pen-type syringe having a thin needle that makes the patients feel little pain has been developed. Type I diabetic patients often work like able-bodied persons except that the patients must periodically take insulin. It is difficult for such a patient to take insulin at proper times because he/she feels dislike to make an inject in the presence of others even with a pen-type syringe.

Under the circumstances, a method of discharging a medicine in the form of droplets and making them reach the lungs together with inhaled air, thereby administering the medicine through the lungs instead of injection.

In such an inhalation scheme, however, since the amount of air inhaled and inhalation rate vary among patients, it is difficult to efficiently administer medicines to all patients. For this reason, this scheme is no practical use.

Assume that patients can easily administer medicines by themselves. In this case, problems are posed concerning how to handle an instance where a patient takes a wrong medicine or does not take a proper amount of medicine or at wrong intervals.

A terminal used in the conventional medical system is designed to be installed in user's home but not to be carried. If, therefore, the condition of a patient becomes worse or suddenly changes on the road, a proper treatment cannot be provided.

This also applies to insurance systems in operation. More specifically, in receiving a medical consultation or treatment in a medical facility, a patient generally presents a health insurance card in Japan or an ID card issued by an insurance company in the USA. However, the contents written on such an insurance card or ID card do not include any necessary information for an emergency.

For example, the contents written on a health insurance card in Japan include only the name of the patient himself/herself, the names of dependents, address, the name and location of company, the type of insurance, insurance card number, and medical treatment record (brief clinical history), but do not include any information about a clinical chart, prescription, and the like. The contents written on an ID card in the USA include only an individual number, insurance details, and the like but do not include any information about a clinical chart or prescription either.

For this reason, demands have arisen for a method of accurately and efficiently performing medical consultation and treatment on the basis of a database for managing information about individual clinical charts and medical information as electronic data.

SUMMARY OF THE INVENTION

The present invention has been made in consideration of the above situation, and has as its first object to provide a health management method and system using a portable terminal, which can properly and quickly handle an emergency in cooperation with a database storing various pieces of medical information.

It is the second object of the present invention to provide a portable terminal having an inhaler, and a control method for the inhaler, which can accurately manage medicines in accordance with prescriptions and perform discharging control suitable for each user, thereby efficiently administering medicines.

It is the third object of the present invention to provide a health management method and system using a portable terminal, which can perform efficient medical practices by sharing information while protecting personal data associated with privacy.

It is the fourth object of the present invention to provide a portable terminal having an inhaler and a method of driving the inhaler, which can improve the inhalation efficiency when the inhaler discharges a medicine.

It is the fifth object of the present invention to provide a method and system for supporting determination of a prescription, which allow proper and efficient determination of a prescription applied to each patient and a medicine to be administered.

It is the sixth object of the present invention to provide an inhaler and a discharge head control method, which can prevent a patient from loading a wrong medicine and erroneously operating the inhaler, and also allows the patient to accurately and easily take a medicine by himself/herself.

In order to achieve the first object, according to the first aspect of the present invention, there is provided a health management system for managing health of each user carrying a portable terminal, comprising a portable terminal which is arranged to be carried by a user and includes a display screen, radio communication means for accessing a predetermined radio communication network, storage means storing personal information of the user, and an input/output device for supporting health management for the user, and a database including personal information storage means storing the personal information about each user carrying the portable terminal, medical information storage means storing information about a medical facility, a drugstore, a medicine, and the input/output device, and communication means for communicating with the portable terminal through the radio communication network, wherein the radio communication means transmits part of the personal information stored in the storage means in starting to communicate with the database, and the database includes identification means for identifying the user of the portable terminal by collating the part of the information transmitted from the radio communication means with information stored in the personal information storage means, and emergency handling means which is activated upon transmission of a specific signal from the radio communication means to communicate with a medical facility whose information is stored in the medical information storage means in accordance with information transmitted from the radio communication means and to provide the portable terminal with information, of the information stored in the medicine information storage means, which is necessary for the identified user.

In addition, in order to achieve the first object, according to the first aspect of the present invention, there is a health management method of managing health of each user carrying a portable terminal, including providing the portable terminal with a display screen, radio communication means for accessing a predetermined radio communication network, storage means storing personal information of the user, and an input/output device for supporting health management for the user, providing a database for communicating with each portable terminal with personal information storage means storing the personal information about each user carrying the portable terminal, medical information storage means storing information about a medical facility, a drugstore, a medicine, and the input/output device, and communication means for communicating with the portable terminal through the radio communication network, transmitting part of the personal information stored in the storage means by the radio communication means when starting to communicate with the database, identifying in the database, the user of the portable terminal by collating the part of the information transmitted from the radio communication means with information stored in the personal information storage means, and providing one of communication with a medical facility whose information is stored in the medical information storage means and information stored in the medicine information storage means, which is necessary for the identified user for the portable terminal when a specific signal is transmitted from the radio communication means.

With the arrangement or processing of the first aspect of the invention, when a specific signal is transmitted from the portable terminal, the user of the portable terminal is identified to allow the user to communicate with an medical facility or to provide the identified user with necessary information, thereby properly and quickly handling an emergency.

In order to achieve the second object, according to the second aspect of the present invention, there is provided a portable terminal which is arranged to be carried by a user and includes storage means storing personal information about the user, including information about a clinical chart of the user and prescription, and an inhaler for discharging a medicine in the form of fine droplets and making the user inhale the droplets, comprising discharging control means for controlling the inhaler in accordance with an inhalation profile of the user to discharge the medicine, thereby allowing the user to inhale the medicine in accordance with the information of the prescription.

In addition, in order to achieve the second object, according to the second aspect of the present invention, there is provided a control method for an inhaler for discharging a medicine in the form of fine droplets and making a user inhale the droplets, the inhaler being provided for a portable terminal which is arranged to be carried by a user and includes storage means storing personal information about the user, including information about a clinical chart of the user and prescription, and the method including the step of controlling the discharge of the medicine in accordance with an inhalation profile of the user, thereby allowing the user to inhale the medicine in accordance with the information of the prescription.

With the arrangement or the processing of the second aspect of the invention, the dose of medicine and administration intervals can be accurately managed in accordance with a prescription, and proper discharging control is performed in accordance with the inhalation profile of each user, thereby efficiently administering a medicine.

In order to achieve the third object, according to the third aspect of the present invention, there is provided a health management system for managing health of each user carrying a portable terminal, comprising a portable terminal which is arranged to be carried by a user and includes radio communication means for accessing a predetermined radio communication network, storage means storing personal information of the user, and an input/output device for supporting health management for the user, a database including personal information storage means storing the personal information about each user carrying the portable terminal, medical information storage means storing information about a medical facility, a drugstore, a medicine, and the input/output device, and communication means for communicating with the portable terminal through the radio communication network, a medical facility terminal installed in each medical facility and connected to the database through a predetermined line, and a drugstore terminal installed in each drugstore and connected to the database through a predetermined line, wherein the database sets an access right for each item of information stored in the personal information storage means and medical information storage means with respect to each of the portable terminal, the medical facility terminal, and the drugstore terminal.

In addition, in order to achieve the third object, according to the third aspect of the present invention, there is provided a health management method of managing health of each user carrying a portable terminal by using a portable terminal which is arranged to be carried by a user and includes radio communication means for accessing a predetermined radio communication network, storage means storing personal information of the user, and an input/output device for supporting health management for the user, a database including personal information storage means storing the personal information about each user carrying the portable terminal, medical information storage means storing information about a medical facility, a drugstore, a medicine, and the input/output device, and communication means for communicating with the portable terminal through the radio communication network, a medical facility terminal installed in each medical facility and connected to the database through a predetermined line, and drugstore terminal installed in each drugstore and connected to the database through a predetermined line, wherein the method comprises the step of setting an access right in the database, for each item of information stored in the personal information storage means and medical information storage means with respect to each of the portable terminal, the medical facility terminal, and the drugstore terminal.

With the arrangement or the processing of the third aspect of the invention, efficient medical practices can be expected by storing various personal data and medical data as electronic data in the database and sharing the information while protecting personal data associated with privacy by setting an access right for each terminal.

In order to achieve the fourth object of the present invention, according to the fourth aspect of the present invention, there is provided a portable terminal which is arranged to be carried by a user and includes storage means storing personal information about the user, including information about a clinical chart of the user and prescription, and an inhaler for discharging a medicine in the form of fine droplets and making the user inhale the droplets, comprising driving control means for changing a parameter associated with discharging of the medicine within a predetermined period of time in which the user executes the inhalation so as to allow the user to efficiently inhale the medicine in accordance with the information of the prescription.

In addition, in order to achieve the fourth object of the present invention, according to the fourth aspect of the present invention, there is provided a method of driving an inhaler of a portable terminal which is arranged to be carried by a user including providing storage means storing personal information about the user, including information about a clinical chart of the user and prescription, and an inhaler for discharging a medicine in the form of fine droplets and making the user inhale the droplets, with the portable terminal, and changing a parameter associated with discharging of the medicine within a predetermined period of time in which the user executes the inhalation so as to allow the user to efficiently inhale the medicine in accordance with the information of the prescription.

With the arrangement or the processing of the fourth aspect of the invention, when the inhaler is made to discharge a medicine, the parameter associated with discharging of the medicine is changed in accordance with, for example, the inhalation rate. This can improve the inhalation efficiency by sending a larger amount of medicine to the lungs.

In order to achieve the fifth object, according to the fifth aspect of the present invention, there is provided a prescription determination support system including a memory card storing personal information including information about a clinical chart of each user and prescription, a database having medical information storage means storing information about correspondence between a symptom and a medicine prescription, and a medical facility terminal which is installed in each medical facility, has a slot in which the memory card is inserted, and is connected to the database through a predetermined line, the prescription determination support system being adapted to support determination of a prescription for the user carrying the memory card at the medical facility terminal, wherein when the memory card of the user is inserted into the medical facility terminal, the terminal presents information about a prescription suitable for the user and a medicine to be administered on the basis of the personal information about the user and the information stored in the medical information storage means.

In addition, in order to achieve the fifth object, according to the fifth aspect of the present invention, there is provided a prescription determination support method of supporting determination of a prescription for a user carrying a memory card at a medical facility terminal by using the memory card storing personal information including information about a clinical chart of each user and prescription, a database having medical information storage means storing information about correspondence between a symptom and a medicine prescription, and the medical facility terminal which is installed in each medical facility, has a slot in which the memory card is inserted, and is connected to the database through a predetermined line, wherein the method comprises the step of presenting information about a prescription suitable for the user and a medicine to be administered is presented on the basis of the personal information about the user and the information stored in the medical information storage means, when the memory card of the user is inserted into the medical facility terminal.

With the arrangement or the processing of the fifth aspect of the invention, a prescription to be applied to each user and a medicine to be administered to each user can be properly and efficiently determined by using information about the clinical chart and prescription of each user and information about the correspondence between a symptom and a medicine prescription.

In order to achieve the sixth object, according to the sixth aspect of the present invention, there is provided a inhaler for discharging a medicine in the form of fine droplets and allowing a user to inhale the medicine, comprising storage means storing personal information about the user including information about a prescription for the user, a tank which contains the medicine and has a code for identifying a type of contained medicine, a discharge head for discharging a medicine supplied from the tank in the form of fine droplets, and discharge permission means for permitting operation of the discharge head only when a collation result on the medicine contained in the tank and a medicine written on the prescription indicates coincidence upon reading the code.

In addition, in order to achieve the sixth object, according to the sixth aspect of the present invention, there is provided a discharge head control method for an inhaler comprising providing the inhaler with storage means storing personal information about a user including information about a prescription for the user, a tank which contains the medicine and has a code for identifying a type of contained medicine, and a discharge head for discharging a medicine supplied from the tank in the form of fine droplets, wherein said method comprises the steps of collating the medicine contained in the tank with a medicine written on the prescription upon reading the code, and enabling operation of the discharge head only when the collation result indicates coincidence of the both.

With the arrangement or the processing of the sixth aspect of the invention, in administering a medicine by using the inhaler, a patient can be prevented from loading a wrong medicine and erroneously operating the inhaler, and the patient can accurately and easily take a medicine by himself/herself.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specifications, illustrate embodiments of the invention and, together with the description, serve to explain the principles of the invention.

FIGS. 2A and 2B views showing data to be handled in the embodiment shown in FIG. 1;

FIG. 3 is a block diagram showing the arrangement of a user terminal in the embodiment shown in FIG. 1;

FIG. 9 is a view for explaining an emergency notification mode; and

FIG. 10 is a flow chart showing processing for an inpatient.

DETAILED DESCRIPTION OF THE PREFERRED EMBODIMENTS

Preferred embodiments of the present invention will now be described in detail in accordance with the accompanying drawings. As an embodiment of the health management system of the present invention, a medical health management system will be described.

[Overall Arrangement]

Figure 1:
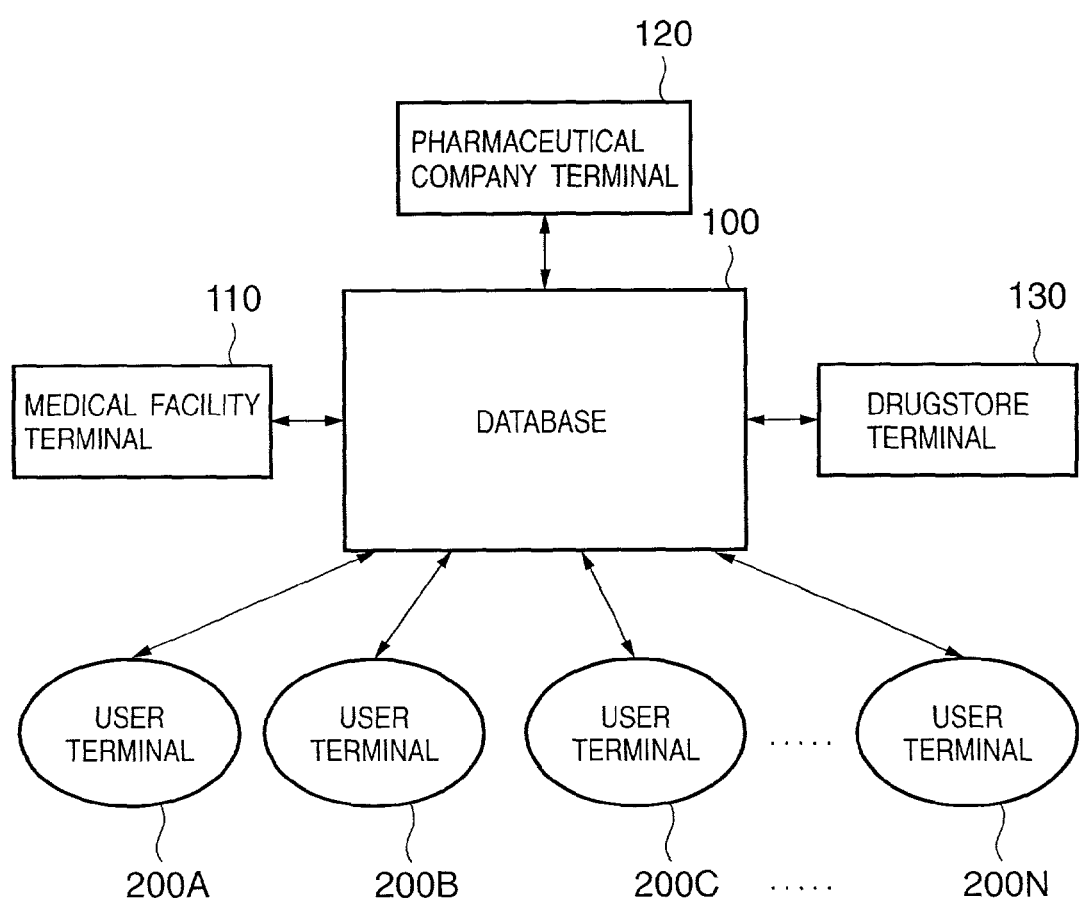
FIG. 1 is a block diagram showing the overall arrangement of a medical health management system according to an embodiment of the present invention.

FIG. 1 is a block diagram showing the overall arrangement of a medical health management system according to this embodiment. As shown in FIG. 1, this embodiment is comprised of a database 100, medical facility terminal 110, pharmaceutical company terminal 120, drugstore terminal 130, and user terminals 200A to 200N. FIG. 1 shows one each of the database 100, medical facility terminal 110, pharmaceutical company terminal 120, and drugstore terminal 130. Obviously, however, this arrangement is merely an example, and each component may include a plurality of identical ones. In addition, FIG. 1 shows only the four user terminals 200A to 200N (to be generically referred to as a user terminal 200 hereinafter). In practice, however, many user terminals are connected.

FIGS. 2A and 2B are views showing data to be handled in this embodiment. As shown in FIG. 2A, the embodiment handles the following data as data about each individual to be registered: basic data including an address, name, date of birth, contact, occupation, place of employment, and the like, identification data including an ID (a number if numbers are assigned to all the people; otherwise, an insurance card number or the like), personal code number, alphanumeric characters such as a password, and biometrical authentication data such as fingerprint, voiceprint, palmprint, face, iris, or retinal blood vessel pattern, health insurance data including a number, type, usage log, and the like, electronic medical and prescription data (electronic clinical chart) for each individual, including a consultation record, prescription, medication data, hospitalization record, case history, family case history, and the like, and data of measurement values obtained by a health examination. Data of a designated medical facility as the emergency contact and inhaler set data (to be described later) are also handled as personal data.

In addition, as shown in FIG. 2B, data handled as medical data are: medical facility data including a registration number, location, contact, registered doctors, facilities, and the like, pharmaceutical company data including a registration number, location, contact, medicines handled, scale, and the like, drugstore data including registration number, location, contact, medicines handled, pharmaceutist name, and the like, drug data including a drum name, effects, cautions, and the like, and inhaler data (not shown) including data about handling and maintenance of an inhaler.

All these data are stored in the database 100. The data about each individual are also stored in each user terminal 200 in the form of a detachable memory card.

The database 100 is a medical database that is installed within, for example, a predetermined range, e.g., an administrative area, and serves to store personal data of each resident in this area and medical data. This database 100 may be installed in a special facility or designated special hospital in the administrative area. The respective databases are connected to each other so that when a given resident is to receive a medical treatment in an area other than the residence area or moves from the residence area, access to necessary data can be made.

The medical facility terminal 110 is installed in each medical facility and connected to the database 100. The medical facility terminal 110 has a slot in which the memory card of the user terminal 200 is inserted. In a consultation, a doctor or nurse working at the medical facility inserts the memory card of the user terminal 200 carried by the patient into the medical facility terminal 110 to read out personal data about the patient who has visited for a medical examination so as to use the data as reference data for the consultation. The doctor or nurse also updates the data in the database 100 and the data of the electronic clinical chart in the memory card of the patient on the basis of the consultation result.

The prescription data to be recorded at this time includes an expiration date. When the patient takes a consultation again within the expiration date, a new expiration date is set as needed.

In the consultation, the doctor refers to medicine data as sell as the personal data about the patient. If the patient suffers a complication (e.g., suffers a visceral disease and cardiovascular disease at the same time), the doctor uses the above data as reference data in making a determination on prescription contents that are competitive. In such a case, the doctor may give the patient the information (informed consent) to give priority to the prescription desired by the patient.

If the DNA analysis result on each patient is recorded on the memory card of the patient or database 100, a prescription can be determined by using techniques called gene diagnosis and gene therapy instead of the conventional average/statistical techniques.

The pharmaceutical company terminal 120 is installed in each pharmaceutical company and connected to the database 100. A person who works at the pharmaceutical company accesses the database 100 from this terminal to check inventory data about medicines in a medical facility or drugstore and update the shipment data of medicines that are supplied. In addition, he/she processes production control data on the basis of these data.

The drugstore terminal 130 is installed in each drugstore and connected to the database 100. This terminal has a slot in which the memory card of the user terminal 200 is inserted. A person who works at the drugstore inserts the memory card of the user terminal 200 carried by a customer into the drugstore terminal 130 to read out customer's prescription data. In addition, the person accesses the database 100 from this terminal to read out the prescription data on the customer who has visited the drugstore and collate the data with the corresponding data in the database 100. When the two data coincide with each other, he/she sells the corresponding medicine to the customer. The person then updates the medication data in the database 100 and customer's memory card on the basis of the sold medicine.

In this case, if the ID or biometrical authentication information of a person who acts as an alternate is registered in the database 100 in advance, a family member, caretaker, or the like, other than the patient himself/herself, can receive a medicine.

If the user makes a contract for electronic commerce (EC) with a financial facility in which the user has an account, a credit card company, or the like in advance, he/she can make a payment through the user terminal 200 in purchasing a medicine without actually paying for the medicine on the spot. This applies to charges for a consultation and medicine which are paid to a medical facility.

The user terminal 200 is compact and lightweight to allow the user to always carry it. Each terminal is made to correspond to a specific individual and incorporates a detachable memory card storing data about the user himself/herself as described above. The terminal has a radio communication function and an input/output device for supporting user's health management, and is connected to the database 100 by radio communication, as needed.

[User Terminal]

FIG. 3 is a block diagram showing the arrangement of the user terminal 200. The user terminal 200 of this embodiment includes a controller 201 including a CPU for controlling the overall terminal, an inhaler 202 serving as an input/output device for supporting user's health management, a communication unit 203 for supporting radio communication, an internal memory 204 storing control programs and various data, a memory card 205 storing personal data, an I/O interface 206, key switches 207 including a ten-key pad and various switches such as an emergency notification (emergency) switch, a display/speech output unit 208 including a liquid crystal display, microphone, speaker, and the like, a sensor 209 for biometrical authentication, and a rechargeable battery (not shown) serving as a power supply such as a secondary battery.

The inhaler 202 includes a tank 2022B in which a predetermined amount of liquid medicine is stored, a discharge head 2022A for discharging the medicine, supplied from the tank, in the form of fine droplets or microdroplets, a control unit 2021 for driving/controlling the cartridge 2022, and a sensor 2023 for reading a code attached to a cartridge or tank or detecting the condition of inhaling (negative pressure) of the user. The inhaler 202 discharges a liquid medicine in the form of fine droplets on the basis of the ink-jet scheme using heat to form mist or aerosol. When the user inhales it, the medicine is administered to the user's body through the lungs.

This administration method replaces the administration method using a syringe to facilitate administration of a medicine by a patient himself/herself and reduce his/her mental and physical burdens.

The communication unit 203 is arranged to perform speech communication based on a proper communication scheme using the ten-key pad of the key switch 207 and the display/speech output unit 208 and communicate data with the database 100 by radio.

Although the radio communication scheme to be used is not specifically described, the scheme used in a currently available mobile communication system (e.g., the cell phone system, PHS system, or car phone system), a satellite system, or a Bluetooth system may be used.

The internal memory 204 may be a read-only medium such as a ROM or a programmable storage medium to allow the user to update or change a program through the communication unit 203.

The memory card 205 is at least re-recordable, detachable storage medium such as a semiconductor storage medium, MO, CD-R, CD-RW, or compact magnetic disk.

The I/O interface 206 is designed to selectively connect external input/output devices 250 such as various measurement sensors and printers when the user is to measure a blood pressure, pulse, blood glucose level, bodily temperature, urine protein, or the like or print his/her measurement data.

The user terminal 200 in this embodiment is integrated with the inhaler 202. However, this inhaler 202 may be a detachable discrete device serving as one of the external input/output devices 250 like other medication devices and the above measurement sensors.

The authentication sensor 209 is a sensor for performing biometrical authentication with respect to the user by using a fingerprint, voiceprint, palmprint, face, iris, retinal blood vessel pattern, or the like to allow only the registered person to use the user terminal 200.

Although not shown, the user terminal 200 has a navigation function of detecting the current position of the terminal by using the intensity of a radio wave received from a GPS or a base station in a radio telephone network and indicating a route to a nearby medical facility or drugstore by using map information.

[Security Measures]

The medical health management system of this embodiment must be configured to satisfactory protect data because the data handled by the system are about privacy and important medical data. In addition, to prevent any medical malpractice and operation error, this system must be configured to perform failsafe operation.

For example, data is preferably stored in the database 100 by a scheme that allows only additional writing (additional recording). However, a specific person in charge may overwrite certain old data upon backing up the data to another storage medium. In order to suppress an excessive increase in the necessary capacity of the memory card of the user terminal 200, data that has aged a predetermined number of years may be overwritten.

The database 100 sets an access right for each data item with respect to each of the terminals to which the database 100 is connected, including the medical facility terminal 110, pharmaceutical company terminal 120, drugstore terminal 130, and user terminal 200.

More specifically, the medical facility terminal 110 can access all the data in the database 100, but can write only part of the data about the medical facility, the data of a usage log of the health insurance card carried by a patient who has visited the medical facility, the data of a clinical chart, and the data of measurement values obtained by a health examination and the like. The drugstore terminal 130 can access personal prescription data and medication data when the memory card of the user terminal of the customer is inserted in the drugstore terminal and the IDs coincide with each other, but can normally access only data about medicines and data about pharmaceutical companies. The drugstore terminal 130 can access only data about medicines and data about inventory conditions in medical facilities and drugstores.

In addition, an ID, personal code number, password, and the like must be input to operate each of these terminals. Biometrical authentication may also be performed by using a sensor similar to that of the user terminal 200.

Since the database 100 is connected to the user terminal 200 by radio, especially strict security measures must be taken. The user terminal 200 can access only the personal data about the user and can write only a usage log of medicines (medication data) and data obtained by measurement done by the user himself/herself. When the user accesses the database 100 from the user terminal 200, biometrical authentication is performed by using the authentication sensor 209 in addition to authentication using alphanumerical characters such as an ID, personal code number, password. In communicating data, an encryption technique is preferably used to prevent leakage and tapping (eavesdropping).

In this embodiment, security measures are also taken for medicines prescribed to the user to prevent a usage error, medication error, and operation error.

Every time medication is performed by using the inhaler 202 of the user terminal 200, the cartridge 2022 or tank 2022B is exchanged with a new one. Therefore, each cartridge or tank is packaged independently to allow the user to easily discern whether it is opened or not. One of the above components may be exchanged with a new one for each medication in accordance with the medicine or discharge method to be used. For the sake of simplicity, however, assume that the tank 2022B is exchanged.

When only a tank is exchanged for each medication, a discharge head is used a plurality of number of times. In order to ensure high discharge performance, however, when a given cartridge is used a predetermined number of times or a predetermined period of time has elapsed after the cartridge is loaded, a warning that prompts the user to exchange the cartridge with a new one is preferably provided by picture or sound. In addition, the discharge head is preferably designed such that a heater for generating heat energy is disconnected to inhibit the user from performing actual inhaling operation. When a new cartridge is loaded, the user is made to input his/her ID or password so as to be authenticated again.

Wrong medicine administration is preferably prevented in the following manner. An optically or electrically readable code is attached the tank 2022B. When the tank 2022B is loaded into the user terminal 200, the information of the code is collated with the medicine data written on the electronic clinical chart stored in the memory card 205. If a tank containing a medicine contradicting with the electronic clinical chart is loaded, the patient tries to take a medicine in amount exceeding the dose designated by a doctor, or the patient takes a medicine at improper intervals, a warning is provided by picture or sound, and actual inhaling operation is inhibited.

Attaching a similar code to the cartridge 2022 can also effectively prevent a wrong cartridge from being loaded. In addition, since each cartridge has an electrical terminal for connection to the control unit 2021, the type of cartridge may be identified by using this terminal.

If a used tank is refilled with a medicine and reused, a deterioration in the purity of the medicine or bacterial contamination may occur. This can be effectively prevented as follows. The outer wall of a tank is made of a metal so as to prevent refilling or the above code is overwritten or rewritten to prevent a read of the code after a medicine is used. Alternatively, tanks or medicines themselves may be colored in different colors for the respective prescriptions to allow the user to easily identify them, or the entire inhaler portion is exchanged with a new one in using a different medicine to prevent mixture of medicines.

Furthermore, to perform administration of a medicine at proper intervals based on a prescription, the patient is preferably informed of the timing of administration of the medicine by picture, sound, vibration, or the like.

In actually operating the inhaler, the user is preferably made to input his ID or password to authenticate personal identification again. In addition, when the user makes an operation error or a device fault is detected during operation, the operation of the inhaler is preferably stopped immediately for safety.

Since the user terminal in this embodiment is battery-driven, in order to prevent the battery from running out during inhaling operation, the following operation is required. The remaining power of the battery is checked. If one inhaling operation cannot be done with the remaining capacity, inhaling operation is inhibited. Alternatively, the patient must be notified in advance that the battery will run out after a few inhaling operations. In addition, if the remaining capacity of the battery becomes small, the operation mode may be switched to the power save mode in which the power consumption is smaller than that in the normal discharge mode by, for example, prolonging the discharge time.

In addition, in order to protect the discharge surface (nozzle) of the discharge head and maintain high discharge performance from the hygienic viewpoint, the nozzle surface is capped to prevent a medicine residue on the surface from being dried and fixed and also prevent unnecessary medicine from leaking. This cap is preferably integrated with a cap for the inhaler.

[Emergency Notification]

The user terminal 200 in this embodiment is made to enter the emergency notification mode by continuously pressing the emergency notification (emergency) switch on the key switch 207 of the user terminal 200 for a predetermined period of time when the condition of the patient abruptly changes or abnormality occurs.

FIG. 9 is a view showing an example of the contents of the emergency notification mode. As shown in FIG. 9, when the user terminal in this embodiment enters the emergency notification mode, a menu window is displayed. If the user performs no operation for a predetermined period of time after the menu window is displayed, it is determined that a serious condition has occurred, and emergency notification is performed. In this emergency notification mode, an ambulance is automatically called and a notification is automatically made to a preset contact point such as a family member.

The items prepared on the menu screen for emergency notification include a contact to a designated doctor, notification of additional medical contents, designation of emergency treatment contents, navigation, urgent speech communication, and the like.

"Urgent speech communication" is done by the user himself/herself, if he/she can make it, to make a contact to an emergency facility so as to give information about his/her condition or to make a contact to a doctor or family.

"Navigation" is the function of indicating a route to a nearby medical facility or drugstore or the one which can supply the medicine used by the patient on the basis of the medical data stored in the database 100.

[Cartridge and Tank]

A cartridge in this embodiment discharges a medicine in the form of fine droplets on the basis of the ink-jet scheme using heat. This scheme is basically the same as the so-called bubble jet scheme practiced in printing apparatuses like printers. However, this scheme has several characteristic features in a discharge head and tank which differ from those of printing apparatuses.

For example, a discharge head is made of a material plated with gold, ceramic material, or glass material. In addition, the arrangement of discharge openings (nozzles) and the shape of each discharge opening are changed in accordance with the type of medicine discharged and the method of medication (e.g., whether to need to reach the lungs or not).

A medicine to be contained in a tank may be colored to allow the user to visually check the remaining amount, or may be mixed with a saccharide or polysaccharide, which tends to be scorched, in advance to prevent the property of the medicine from being changed by heating. Furthermore, the amount of medicine to be contained in the tank is preferably determined by adding the amount of medicine required for recovery processing performed when a discharge error occurs during operation or performed before or after inhaling operation to the amount of medicine required for one medication so as to leave a certain amount of medicine when discharge operation is properly performed.

A tank in this embodiment has a double structure. That is, an outer wall made of a metal or the like is integrally formed with an inner wall made of a flexible member whose shape changes in accordance with the amount of medicine contained. This tank differs from an ink tank used in the general ink-jet scheme in that it has neither porous absorber inside nor atmosphere communication port.

Tanks are packaged and supplied, for example, a predetermined number of tanks at a time. In this case, instruments and jigs such as droppers and sterile absorbent gauzes for maintaining discharge heads and caps are preferably packaged together.

As described above, in this embodiment, every time medication is performed, the tank 2022B is exchanged with a new one, and the cartridge 2022 is also exchanged after a predetermined number of times of medication or at predetermined intervals. The exchanged cartridges and tanks are effectively recycled in the following manner.

Cartridges and tanks are manufactured by a pharmaceutical company and supplied to patients through pharmacies belonging to medical facilities and ordinary drugstores. As described above, when a patient is to obtain a cartridge or tank, he/she inserts the memory card into the medical facility terminal 110 or drugstore terminal 130. The prescription data stored in the memory card is then collated with the prescription data stored in the database 100. Since medicine data includes the data of a medicine used in the past, whether the patient has already used the same type of cartridge or tank can be easily known.

If the patient has used the same type of cartridge or tank, he/she brings it with him/her and exchanges it with a new one. In this case, if information indicating whether the cartridge or tank has been collected is also recorded as a medicine usage log in the medicine data, collection can be done more reliably.

The cartridge or tank is collected to the pharmaceutical company through a medical facility or drugstore. The outer appearance and function of the cartridge or tank are then checked. The cartridge or tank that can be further used is cleaned, sterilized/disinfected, and refilled with a medicine. After the information of the code on the cartridge or tank is rewritten, it is reused.

[Inhaling Operation]

Processing in actual inhaling operation using the user terminal 200 in this embodiment will be described next with reference to the flow chart of FIG. 4.

First of all, it is checked whether adjustments for the administration of a medicine have been done (step S301). This adjusting operation includes the initialization step of registering data such as the amount of a medicine for one medication and medication intervals (step S302), the test inhaling step of determining discharge conditions by measuring the amount of air inhaled by each user and a profile (step S303), and the decision step of checking whether the adjustments are done properly as a result of the test inhaling (step S304).

This adjusting operation is performed under the guidance of an expert, e.g., a doctor when it is diagnosed that a medicine must be administered. The measured amount of air inhaled, the measured profile, and the determined discharge conditions are stored as inhaler setting data in both the database 100 and the memory card 205 of the user terminal 200.

To perform actual inhaling operation, a cartridge and/or tank are/is loaded into the inhaler 202 (step S305). To allow the user to perform the operation, authentication with respect to the user is then performed on the basis of a combination of one of an ID, personal code number, and password, and a biometrical authentication means such as a fingerprint (step S306).

Before actual inhaling operation, inhalation/recovery processing is performed by using instruments such as an inhaling jig (step S307). The user then holds the discharge opening end of the inhaler in his/her mouth and executes inhaling operation (step S308). The inhaler starts discharging the medicine upon detecting the inhalation by the user with a negative pressure sensor or the like. While the medicine is discharged, the user terminal preferably generates a signal sound or the like. When a predetermined amount of medicine is discharged after the user repeats inhalation several times (step S309), the inhaling operation is terminated. The end of inhalation is preferably informed by signal sound or indication.

[Driving Control of Discharge Operation]

In this embodiment, a liquid medicine is discharged in the form of fine droplets on the basis of the ink-jet scheme using heat. In this scheme, a driving waveform is formed into a pulse-like shape to control the number of droplets discharged on the basis of the number of pulses. This scheme is therefore suited to accurately managing the amount of liquid discharged.

In this embodiment, however, to use this scheme for medical treatment, discharging control is performed differently from that in a printing apparatus. More specifically, the printing apparatus prints by discharging ink downward on a print medium such as a paper sheet. In contrast to this, the inhaler in this embodiment must discharge a medicine in the form of mist or aerosol and make the medicine reach the lungs, together with the air inhaled by the user.

For this reason, control must be performed to decrease the size of each droplet to a size much smaller than that in the general printing apparatus and reliably discharge droplets with such a small size by a proper amount. If the size of each droplet decreases, the kinetic energy of discharged droplets is low. These droplets need not be discharged in almost one direction as in a printing apparatus, and the droplets discharged in various directions may fly and collide with each other.

In this embodiment, therefore, driving parameters are changed in accordance with the profile (pattern) of air inhalation. For example, in inhaling air, the amount of air inhaled per unit time is large at the start time point, and decreases immediately before the end of inhalation. If, therefore, the medicine is to be discharged a plurality of number of times within an inhalation time (one to two sec), different discharging speeds, different driving frequencies, and the like are set for the first discharge operation and the last discharge operation. Alternatively, the discharge scheme, the size of each droplet, and the main droplet/sub-droplet ratio may be changed. The timing at which these driving parameters are changed is preferably stored in the memory card in association with the medicine to be used.

Furthermore, the profiles of air inhalation vary among individuals owing to ages, sexes, physiques, and the like. For this reason, even with the same prescription, the profiles must be finely adjusted (tuned) in accordance with the respective users. This operation will be described with reference to the portion described in association with steps S302 to S304 in the flow chart of FIG. 4.

To check whether inhalation is accurately performed, discharged droplets are preferably monitored by an optical detection means or the like. In this case, if inhalation is not properly performed, a warning is preferably generated. As a detection method, for example, a method of detecting reflected light, refracted light, transmitted light, or scattered light or a coloring matter or fluorescent agent mixed in a medicine or a method using a laser may be used.

[Flow of Medicine]

Figure 5:
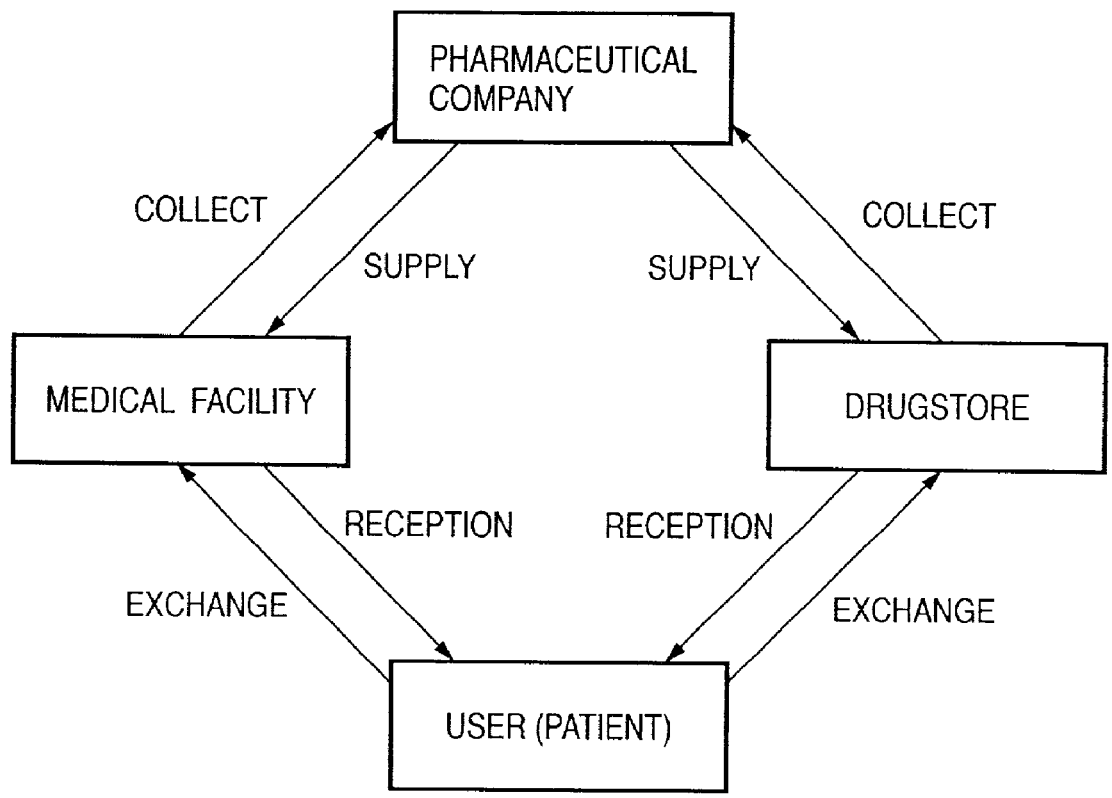
FIG. 5 is a view showing the flow of a medicine in the embodiment shown in FIG. 1.

The flow of a medicine (cartridge and tank) in this embodiment will be described below with reference to FIG. 5.

The medicines manufactured by a pharmaceutical company are supplied to medical facilities and drugstores. Assume that it is required for a user (patient) to take a medicine as a result of consultation with a doctor. In this case, if, for example, the user visits the medical facility for the first time, he/she receives a medicine for a predetermined number of days from the pharmacy of the medical facility from which he/she has taken the consultation.

In the second or subsequent visit with a consultation, the user receives a medicine from the pharmacy of the medical facility in the same manner as described above. At this time, the previously received and used medicine is exchanged with a new one, and the data of the new medicine is written in the medication data on the electronic clinical chart.

If no consultation need be taken, the user may receive the medicine from a drugstore. In this case as well, the previously received and used medicine is exchanged with a new one, and the data of the new medicine is written in the medication data on the clinical chart by using a drugstore terminal.

The used medicine received from the patient is collected from the medical facility or drugstore to the pharmaceutical company and recycled in the above manner.

[Flow of Data]

Figure 6:
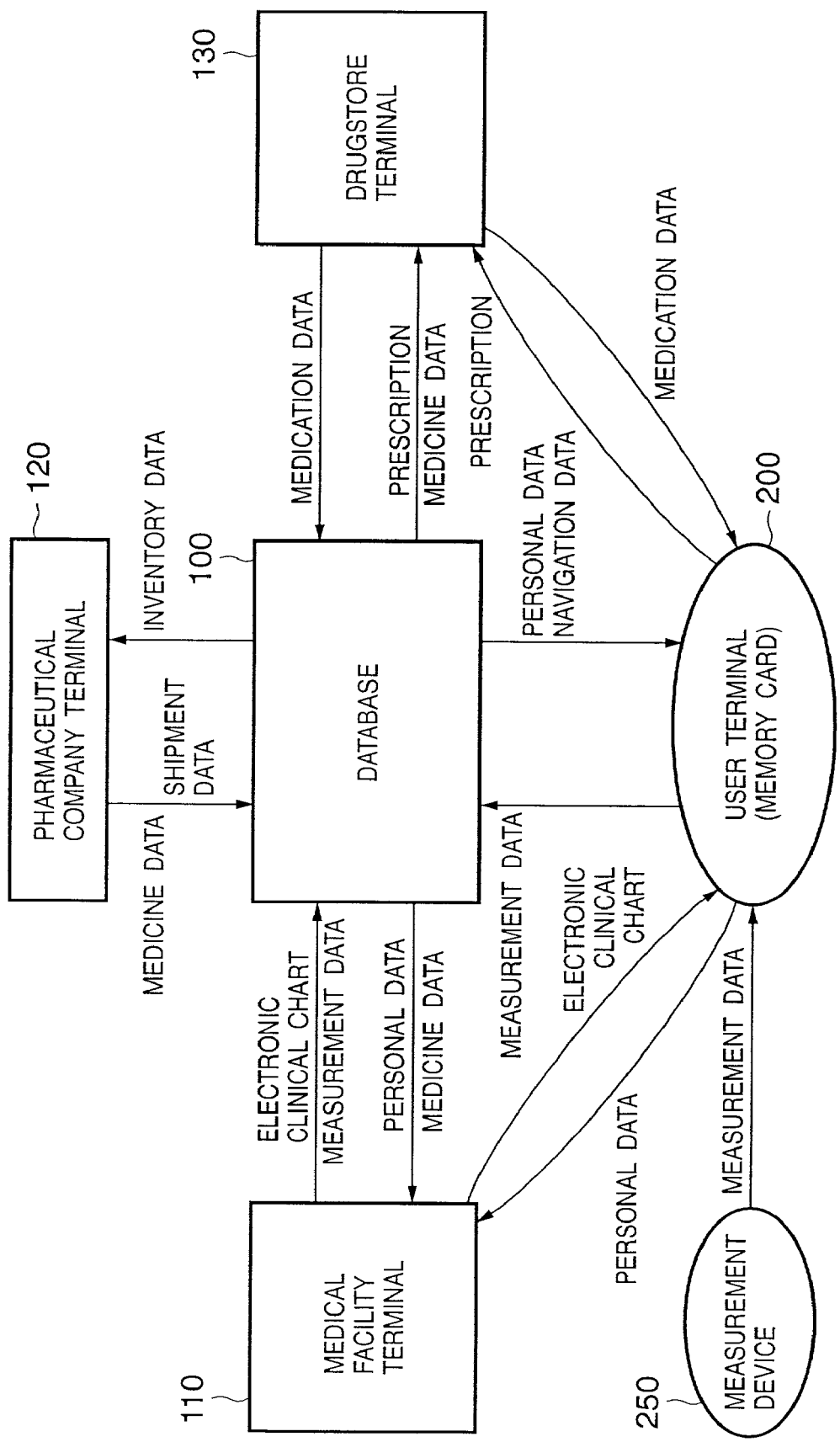
FIG. 6 is a view showing the flow of data in the embodiment shown in FIG. 1.

FIG. 6 is a view schematically showing the flow of data in this embodiment.

As shown in FIG. 6, the health management system according to this embodiment has the database 100 as a main component, which manages data in a centralized manner. The respective terminals also manage necessary information in a decentralized manner.

The medical facility terminal 110 reads out medicine data from the database 100. In a consultation, the medical facility terminal 110 reads out the personal data of the patient from the memory card of the user terminal 200, collates the data with the data read out from the database 100, and writes the data of a health insurance card and electronic clinical chart in the database 100 and the memory card of the patient.

The pharmaceutical company terminal 120 reads out inventory data on medicines in medical facilities and drugstores from the database 100, and writes the data of shipped medicines as shipment data in the database 100. If a new medicine is developed or new effect is found, the pharmaceutical company terminal 120 writes new medicine data in the database 100.

The drugstore terminal 130 reads out prescription data and medication data from the memory card of the user terminal 200 of the patient when he/she visits the drugstore, and collates the data with the prescription read out from the database 100. The medication data about the medicine purchased by the patient is written in the memory card and the database 100.

The measurement data obtained by the patient himself/herself using a medical diagnostic instrument or outside the medical facility is written in the memory card of the user terminal 200 of the patient. This measurement data is written in the database 100, as needed, through the medical facility terminal 110. In addition, in response to a request from the patient, the data of the electronic clinical chart or navigation data about a nearby medical facility or drugstore is read out from the database 100.

SPECIFIC EXAMPLES

Specific examples of how health management is performed for several patients by using the health management system according to this embodiment will be described below.

Assume that in the following specific examples, each patient has already possessed the user terminal 200 having a memory card which is issued by a public facility such as a public office or a medical facility from which the patient has taken a period medical checkup and stores basic data, identification data, health insurance data, and measurement data.

(1) Insulin-treated Patient

Figure 7:
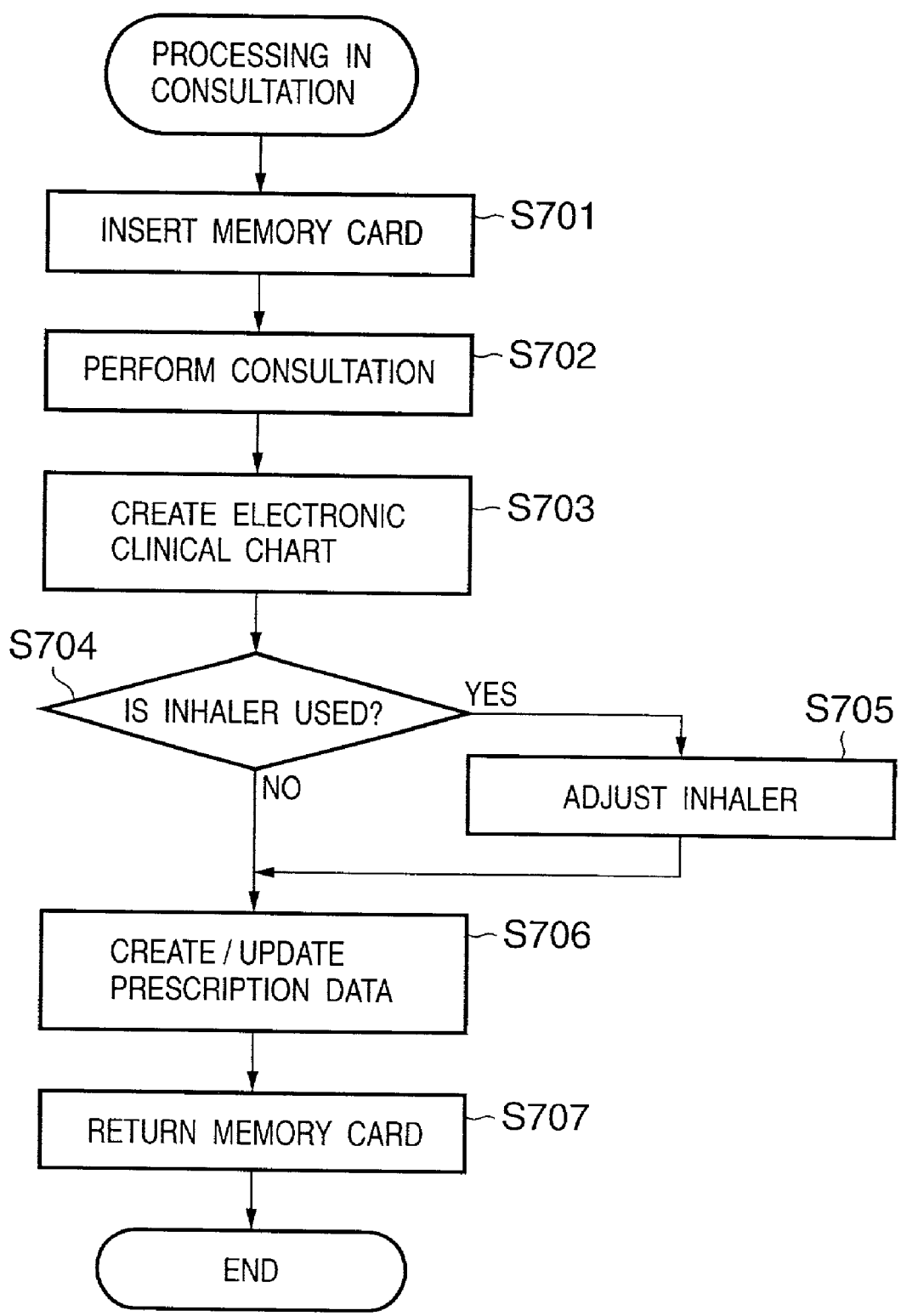
FIG. 7 is a flow chart showing processing in a consultation using a medical facility terminal.
Figure 8:
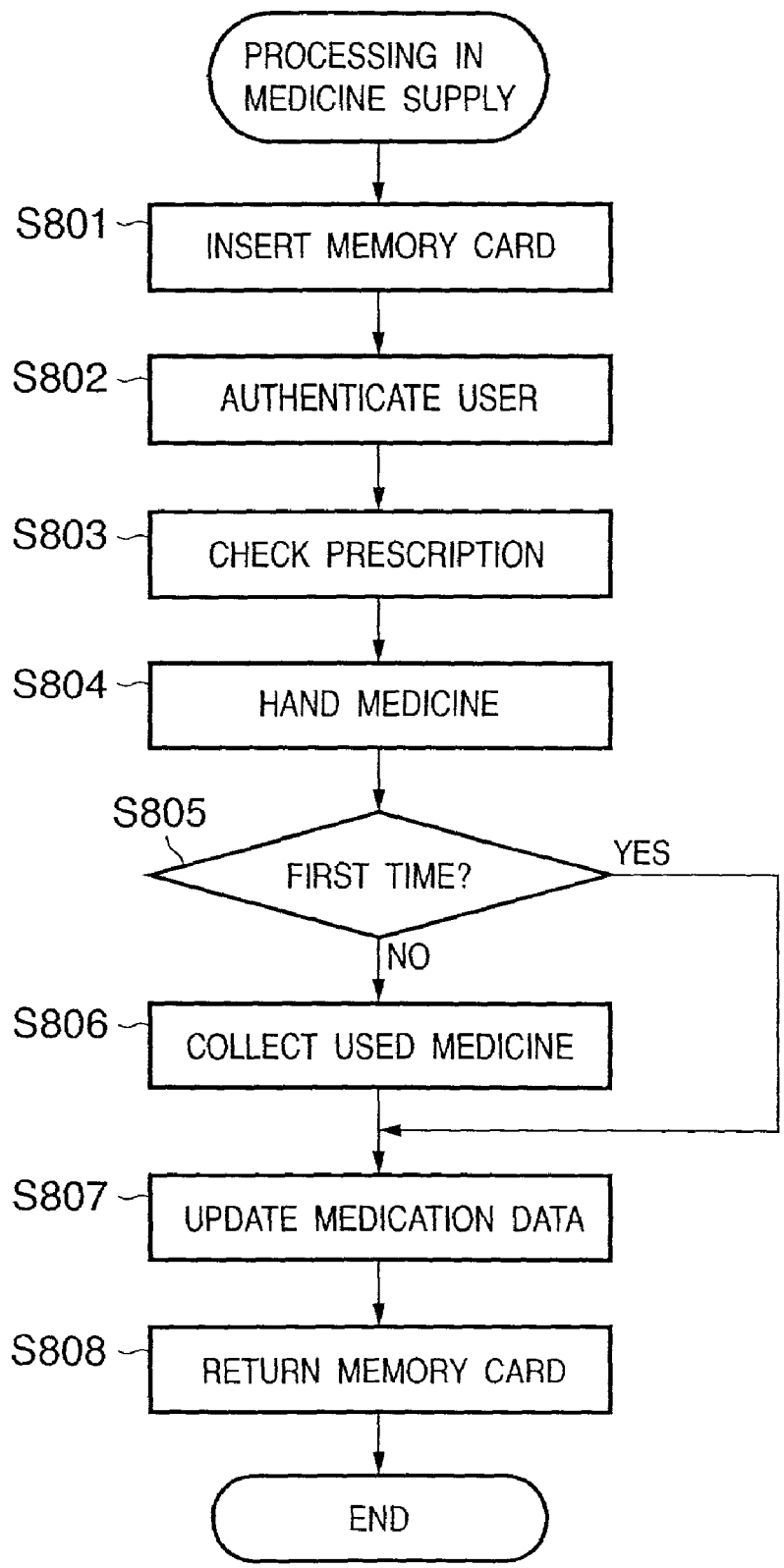
FIG. 8 is a flow chart showing processing in medicine supply.

The flow charts of FIGS. 7 and 8 show examples of processing to be performed when a consultation is performed and a medicine is supplied, respectively. An example of a patient who needs insulin treatment will be described below with reference to these flow charts.

A patient A was told in a periodic medical checkup that his/her blood glucose level was high, and hence visited a nearby medical facility to take a consultation. The patient removed the memory card from this/her user terminal and handed it to a doctor. The doctor inserts the patient's memory card into an medical facility terminal (step S701). The patient then consulted the doctor (step S702). As a result of the consultation, this case was diagnosed as type I insulin-dependent diabetes mellitus, and the patient must periodically medicated with insulin. As a medicine to be prescribed, a mixed formulation of an intermediate type medicine and an immediate type medicine is determined, and the patient was obliged to take 20 units of each medicine within 30 min before breakfast and dinner. Upon consulting with the doctor, standard intake times were set, and an electronic clinical chart was formed (step S703).

The data of this electronic clinical chart was written in the memory card of the user terminal 200 of the patient and the database 100. At this time, the data of a photograph of the patient's face and a fingerprint of the patient were newly written as authentication data. The patient A selected pulmonary inhalation as a method of taking insulin (step S704), and would use the inhaler of the user terminal 200 for the first time.

Figure 4:
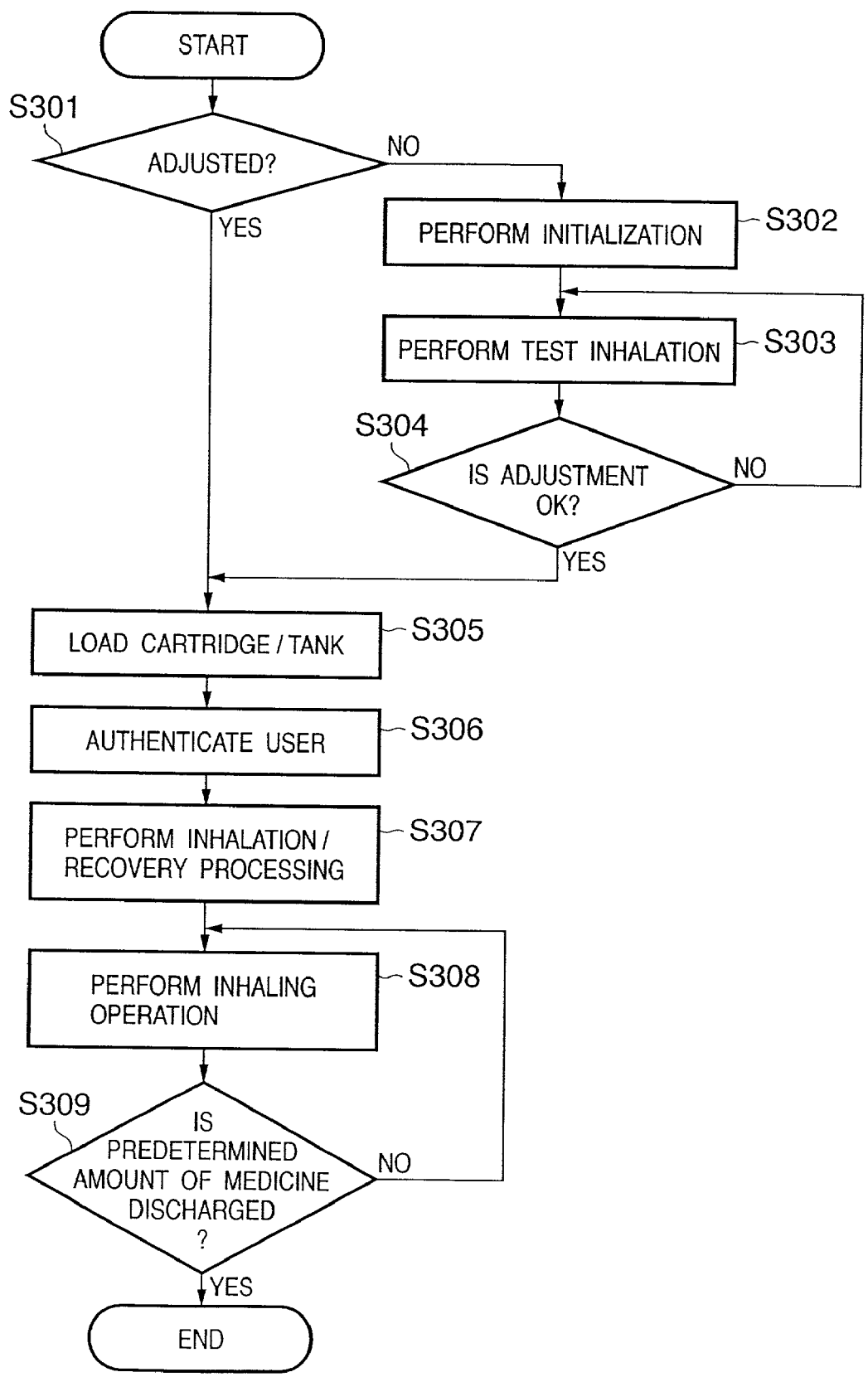
FIG. 4 is a flow chart showing inhaling operation using the user terminal shown in FIG. 3.

As described in association with steps S302 to S304 in FIG. 4, the inhaler setting data about the patient A was registered in the memory card and database under the guidance of the doctor (step S705).

Upon completion of the above processing, prescription data was created/updated (step S706), and the patient's memory card was removed from the medical facility terminal and returned to the patient (step S707), thus terminating the processing at the time of consultation.

The patient A went to the pharmacy of the medical facility while carrying the user terminal 200 to receive a medicine. The patient handed his/her memory card to a person in charge in the pharmacy, and the person inserted the memory card into the medical facility terminal in the pharmacy (step S801) to authenticate the patient with an ID and fingerprint (step S802). The person then checked the prescription data in the memory card by collating it with the prescription data in the database (step S803). If the data do not coincide with each other in step S802 or S803, the processing is interrupted, and the prescription is informed of the corresponding information.

Since the data coincided with each other in steps S802 and S803, the person in charge handed insulin for one month to the patient A (step S804). This insulin is contained in a cartridge, and the medicine box that the prescription has received also contains an inhaling jig. It was checked that this medicine was supplied for the first time (step S805). Information such as the amount of insulin received, date, expiration date, intervals, and the like is written as medication data in both the memory card and the database (step S807). The memory card was then removed and returned to the patient (step S808).

When the patient A returned home, a warning sound indicating a standard setting time was generated, and the patient A took out one of cartridges, each of which was packaged, from the received medicine box. The patient carefully opened the package and confirmed that no medicine leaked. The patient then loaded the cartridge into the inhaler. When the cartridge was mounted, the user terminal collated the prescription data written on the electronic clinical chart in the memory card with the information of the loaded cartridge and displayed the type of cartridge and the loading time on the display.

As described with reference to steps S306 to S309 in FIG. 4, after the user was authenticated with an ID or fingerprint and inhaling/restoring operation was performed by using a jig, the user inhaled insulin and completed self-administration operation by inhalation. The date when the patient executed inhaling operation was stored in the memory card.

When the patient periodically repeated such inhaling operation for several days, he/her felt ill on the road. The patient then went to a nearby drugstore by using the navigation function of the user terminal, measured his/her blood glucose level, and stored the measurement result in the memory card. Since the measurement value was slightly higher than the normal value, the patient transferred the data stored in the memory card to the database, and contacted the doctor in charge by using the emergency notification function of the user terminal, thus asking for an instruction from the doctor through speech communication.

Another day, the patient went to his/her accustomed drugstore because the insulin on hand began to run out, and found that the drugstore had run out of stock. The patient therefore went to a nearby drugstore having insulin in stock by searching for it using the navigation function. The patient received a new cartridge according to the above procedure described with reference to steps S801 to S804 in FIG. 8. In this case, since this medicine was not supplied for the first time, the flow advanced from step S805 to step S806 to return the used cartridge. At the drugstore terminal, the medication data in the memory card and database were updated, and the inventory data of the medicine was updated. The memory card was then returned to the patient.

(2) Impotentia Erigendi Case

An impotentia erigendi case will be described next with reference to the flow charts of FIGS. 7 and 8.

A patient B went to a medical facility to receive a consultation. The patient removed a memory card from his/her user terminal and handed it to a doctor. The doctor inserts the memory card into an medical facility terminal (step S701) and performed a consultation (step 702). As a result of the consultation, the patient was diagnosed with impotentia erigendi.

It was then determined on the basis of the consultation with the doctor that the patient would take gonadotrophic hormone by pulmonary inhalation for three months. It was determined that the medicine would be supplied weekly, and the patient would take the medicine at predetermined intervals which were determined by himself/herself as necessary. The above information was written in both the memory card and the electronic clinical chart in the database (step S703).

The inhaler setting data about the patient B were registered in the memory card and database under the guidance of the doctor as described with reference to steps S302 to S304 in FIG. 4 (step S705). At the same time, data of a photo of the face and fingerprint were also written newly as authentication data.

When the above processing was completed, the doctor created/updated prescription data (step S706), removed the patient's memory card from the medical facility terminal, and returned it to the patient (step S707), thus completing the processing in the consultation.

The patient B went to the pharmacy of the medical facility while carrying the user terminal 200, and handed the memory card to a person in charge in the pharmacy. The person in charge inserted the memory card into a medical facility installed in the pharmacy (step S801) to authenticate the patient with the ID and the photo of the face (step S802), and checked the prescription in the memory card by collating it with the prescription in the database (step S803). The person in charge then handed a medicine for one week to the patient B (step S804). This medicine is of a type that is exchanged with a new one in the form of a tank, and the received medicine box also contains an inhaling jig. The person determined that this medicine was supplied for the first time (step S805), and wrote medicine data such as the amount of medicine received, date, expiration date, and intervals in both the memory card and the database (step S807). The person removed the memory card and returned it to the patient (step S808).

The patient B took out the tank from the medicine box and loaded it into the cartridge as needed, and took the medicine by himself/herself by inhalation as in the case of (1) in accordance with a desired effect exertion time.

The received medicine ran out one week after it was received, and hence the patient B went to the drugstore. The patient received a new tank according to the processing described with reference to steps S801 to S804 in FIG. 8. In this case, since the medicine was not supplied for the first time, the flow advanced from step S805 to step S806 to return the used tank. At the drugstore terminal, the medication data and the inventory data of the medicine in the memory card and database were updated, and the memory card was returned to the patient.

(3) Person Who Wants to Quit Smoking

A case of a person who wants to quit smoking will be described next with reference to the flow charts of FIGS. 7 and 8.

A patient C went to a medical facility to have medical treatment with the aim of quitting smoking. The patient removed a memory card from this user terminal and handed it to a doctor. The doctor inserted the patient' memory card into an medical facility terminal (step S701) and made a medical inquiry (step S702). The doctor determined on the basis of the medical inquiry and consultation that the prescription would take a medicine by pulmonary inhalation to reduce the nicotine intake step by step. It was determined that the medicine would be supplied weekly, and the maximum dose per day would be determined in accordance with a predetermined concentration decrease gradient. The above information was written in the memory card and the electronic clinical chart in the database (step S703).

The inhaler setting data about the patient C were registered in the memory card and database under the guidance of the doctor as described with reference to steps S302 to S304 in FIG. 4 (step S705). At the same time, data of a photo of the face and fingerprint were also written newly as authentication data.

In this case, the inhaler is controlled such that when the patient inhales the medicine at predetermined intervals or shorter intervals, the nicotine intake per day decreases, and the patient is inhibited from inhaling the medicine in amount exceeding the maximum dose per day. In addition, the inhaler is controlled such that even if the dose in the previous day is less than the maximum dose, the remaining amount of medicine is not added to the amount of medicine for the next data.

When the above processing is completed, prescription data is created/updated (step S706), and the patient's memory card is removed from the medical facility terminal and returned to the patient (step S707), thus terminating the processing at the time of consultation.

The patient C went to the pharmacy of the medical facility while carrying the user terminal 200, and handed his/her own memory card to a person in charge in the pharmacy. This person inserted the memory card into the medical facility terminal installed in the pharmacy (step S801) to authenticate the patient with the ID and the photo of the face (step S802), and checked the prescription in the memory card by collating it with the prescription in the database (step S803). The person in charge then handed a medicine for one week to the patient C (step S804). This medicine is of a type that is exchanged with a new one in the form of a tank, and the received medicine box also contains an inhaling jig. The person determined that this medicine was supplied for the first time (step S805), and wrote medicine data such as the amount of medicine received, date, expiration date, and intervals in both the memory card and the database (step S807). The person removed the memory card and returned it to the patient (step S808).

The patient C took out the tank from the medicine box several times a day, loaded in into the cartridge, and took the medicine by himself/herself by pulmonary inhalation as in the case of (1) instead of smoking.

The received medicine ran out one week after it was received, and hence the patient C went to another medical facility. A doctor inserted the memory card of the patient C into the medical facility terminal, set the maximum dose per day and the number of times of inhalation for each inhaling operation in accordance with the concentration decrease gradient set by reading out data from the electronic clinical chart of the patient C, and wrote a new prescription. In addition, the inhaler was adjusted in accordance with the new prescription.

The patient received a new tank at the pharmacy of the medical facility according to the processing described with reference to steps S801 to S804 in FIG. 8 as in the above case. In this case, since the medicine was not supplied for the first time, the flow advanced from step S805 to step S806 to return the used tank. At the medical facility terminal of the pharmacy, the medication data and the inventory data of the medicine in the memory card and database were updated, and the memory card was returned to the patient.

(4) Inpatient

A case of an inpatient will be described next with reference to the flow chart of FIG. 10.

In a periodic medical checkup, a stomach cancer in a patient D was found. The patient therefore went to a medical facility to take ablation surgery. In the medical facility, a doctor inserted the patient's memory card into a medical facility terminal (step S1101) to diagnose the case by reading out past medical checkup result and stomach X-ray photograph images, and performed an operation (step S1102).

The doctor created an electronic clinical chart including a medical treatment after the operation on the basis of the operation result (step S1103). The memory card of the patient D was moved to a bed-side terminal attached to a bed in the hospital in which the patient D would stay (step S1104), and persons in charge, e.g., a doctor and nurse, were registered (step S1105).

This bed-side terminal is a modification of the medical facility terminal 110, and has almost the same arrangement as that of the user terminal 200 except that the inhaler 202 is omitted. However, this terminal has a wide display for better viewability. The name of the patient, the name of disease, and the symptom are always displayed on this display screen.

For everyday treatment performed by the doctor or nurse, he/she identifies the patient according to the name and symptom displayed on the display screen (step S1106), and inputs the ID of the doctor or nurse to read out the electronic clinical chart (step S1107). The doctor then makes his rounds or the doctor or nurse performs a necessary check or measurement (step S1108). The prescription data is updated on the basis of the resultant data (step S1109).

When a predetermined period of time has elapsed, the condition of the patient improved, and the patient was given a permission to leave the hospital (step S1110). When the patient left the hospital, the memory card was returned to him/her (step S1111).

Effects of Embodiment

As has been described above, this embodiment has the following effects.

(1) Various personal data and medical data are electronized and stored in the database, and hence efficient medical practices can be expected by information sharing.

(2) Personal data about privacy can be protected by setting an access right for each terminal and personal identification.

(3) Since each user terminal has the emergency notification mode, emergencies can be properly and quickly handled.

(4) Administering a medicine by using the inhaler of a user terminal instead of injection as in the prior art allows a patient himself/herself to easily take the medicine, thus reducing his/her mental and physical burdens.

(5) In discharging a medicine from the inhaler, the driving parameters are changed in accordance with the inhalation rate and the like to send a large amount of medicine to the lungs, thereby improving the inhalation efficiency.

(6) In administering a medicine by using the inhaler, the medicine can be efficiently administered by performing proper discharging control in accordance with the amount of air inhaled by each patient and the profile.

(7) When a patient takes a medicine by himself/herself, the patient can be prevented from loading a wrong medicine or erroneously operating the inhaler.

(8) With the controller of a user terminal, the dose of a medicine and medication intervals can be accurately managed in accordance with prescription data.

(9) Since the supply and administration of medicines are recorded, the medicines used by each patient and inventories can be accurately managed. In addition, used cartridges and tanks can be accurately collected.

(10) Prescription data is also stored in the memory card of each user terminal. This allows each user to receive medicines according to a prescription by reading the data regardless of the area where he/she is located.

(11) The navigation function of each user terminal facilitates access to a nearby or suitable medical facility or drugstore.

Other Embodiment

The above embodiment has exemplified the medical health management system. However, the present invention can be applied to various other applications.

For example, the present invention may be applied to a system for instructing each user to regularly practice diet and exercise for health and beauty in accordance with a preset program by using a user terminal similar to the one described above and a terminal installed in a sports club or the like, or the above inhaler of the user terminal may be used to take proper amounts of vitamins and minerals, other than medicines, which are necessary for health.

When the present invention is used for such an application other than medical applications, the data stored in the database and each terminal and the function of each user terminal are changed as needed.

In addition, the present invention can be used as a medical health management system in such a manner that the above inhaler of the user terminal is used for an inhalation treatment for an asthmatic patient or to administer a medicine into the patient's body, which is currently administered by injection or in the form of an internal medicine.

The arrangement of the health management system is not limited to the above embodiments. For example, the database may be incorporated in the medical facility terminal.

As many apparent widely different embodiments of the present invention can be made without departing from the spirit and scope thereof, it is to be understood that the invention is not limited to the specific embodiments thereof except as defined in the claims.

What is claimed is:

1. A health management system for managing health of each patient carrying a portable terminal, comprising:

a portable terminal which is arranged to be carried by a patient and includes a display screen, radio communication means for accessing a predetermined radio communication network, storage means for storing personal information of the patient, wherein the personal information includes information of a clinical chart of the patient and a prescription of the patient, an input/output device for supporting health management for the patient, and emergency notification means for transmitting to the radio communication network a type of emergency notification specified by the patient from a plurality of types of emergency notifications; and a database including
personal information storage means for storing the personal information about each patient carrying said portable terminal,
medical information storage means for storing information about a medical facility, a drugstore, a medicine, and said input/output device; and
communication means for communicating with said portable terminal through the radio communication network,
wherein said radio communication means transmits part of the personal information stored in said storage means in starting to communicate with said database, and
wherein said database further includes
identification means for identifying the patient of said portable terminal by collating the part of the information transmitted from said radio communication means with information stored in said personal information storage means, and
emergency handling means which is activated when the type of emergency notification is transmitted from said emergency notification means and which provides, in accordance with the type of emergency notification, said portable terminal either with communication or with information, wherein the communication provided to said portable terminal uses said radio communication means to communicate with a medical facility whose information is stored in said medical information storage means, and wherein the information provided to the portable terminal comprises information about a medical facility or a drugstore providing a medicine needed for the identified patient, and wherein the information is selected from information stored in said medical information storage means based on at least one of the clinical chart and the prescription of the patient,
said portable terminal further comprises position information acquisition means for acquiring position information of said terminal, and said emergency handling means causes said portable terminal to display information about a route from a position of said portable terminal to a suitable medical facility or drugstore on said display screen on the basis of the position information transmitted from said position information acquisition means.

2. The system according to claim 1, wherein said radio communication means and said communication means perform encryption/decryption in accordance with a predetermined scheme in transmitting/receiving at least part of the personal information.

3. A health management system for managing health of each patient carrying a portable terminal, comprising:
a portable terminal which is arranged to be carried by a patient and includes
a display screen,
radio communication means for accessing a predetermined radio communication network,
storage means for storing personal information of the patient, wherein the personal information includes information of a clinical chart of the patient and a prescription of the patient,
an input/output device for supporting health management for the patient, and
emergency notification means for transmitting to the radio communication network a type of emergency notification specified by the patient from a plurality of types of emergency notifications; and
a database including
personal information storage means for storing the personal information about each patient carrying said portable terminal,
medical information storage means for storing information about a medical facility, a drugstore, a medicine, and said input/output device; and
communication means for communicating with said portable terminal through the radio communication network,
wherein said radio communication means transmits part of the personal information stored in said storage means in starting to communicate with said database,
wherein said input/output device is an inhaler for discharging a medicine in the form of fine droplets to make the patient inhale the droplets, and the information about said input/output device includes information about handling of said inhaler, and
wherein said database further includes
identification means for identifying the patient of said portable terminal by collating the part of the information transmitted from said radio communication means with information stored in said personal information storage means, and
emergency handling means which is activated when the type of emergency notification is transmitted from said emergency notification means and which provides, in accordance with the type of emergency notification, said portable terminal either with communication or with information, wherein the communication provided to the said portable terminal uses said radio communication means to communicate with a medical facility whose information is stored in said medical information storage means, and wherein the information provided to the portable terminal comprises information about a medical facility or a drugstore providing a medicine needed for the identified patient, and wherein the information is selected from information stored in said medical information storage means based on at least one of the clinical chart and the prescription of the patient, and
wherein said portable terminal further comprises position information acquisition means for acquiring position information of said terminal, and said emergency handling means causes said portable terminal to display information about a route from a position of said portable terminal to a suitable medical facility or drugstore on said display screen on the basis of the position information transmitted from said position information acquisition means.

4. The system according to claim 1, wherein said emergency handling means communicates with an emergency facility when no information is transmitted a predetermined period of time after said emergency handling means is activated.

5. The system according to claim 1, wherein part of the information includes information about biometrical characteristics of the patient.

6. A health management method of managing health of each patient carrying a portable terminal, including the steps of:
providing a portable terminal carried by a patient with a display screen, radio communication means for accessing a predetermined radio communication network, storage means for storing personal information of the patient, an input/output device for supporting health management for the patient, emergency notification means for transmitting to the radio communication network a type of emergency notification specified by the patient from a plurality of types of emergency notifications, wherein the personal information includes information of a clinical chart of the patient and a prescription of the patient;

providing a database for communicating with each portable terminal with personal information storage means for storing the personal information about each patient carrying the portable terminal, medical information storage means for storing information about a medical facility, a drugstore, a medicine, and the input/output device, and communication means for communicating with the portable terminal through the radio communication network;

transmitting part of the personal information stored in the storage means by the radio communication means when starting to communicate with the database;

identifying using the database, the patient of the portable terminal by collating the part of the information transmitted from the radio communication means with information stored in the personal information storage means; and activating, when the type of emergency notification is transmitted from said emergency notification means, an emergency handling means which provides, in accordance with the type of emergency notification, said portable terminal either with communication or with information, wherein the communication provided to said portable terminal uses said radio communication means to communicate with a medical facility whose information is stored in said medical information storage means, and wherein the information provided to the portable terminal comprises information about a medical facility or a drugstore providing a medicine needed for the identified patient, and wherein the information is selected from information stored in said medical information storage means based on at least one of the clinical chart and the prescription of the patient, wherein said portable terminal further comprises position information acquisition means for acquiring position information of said terminal, and, in the step of activating, said emergency handling means causes said portable terminal to display information about a route from a position of said portable terminal to a suitable medical facility or drugstore on said display screen on the basis of the position information transmitted from said position information acquisition means.

7. The method according to claim 6, wherein the radio communication means and the communication means perform encryption/decryption in accordance with a predetermined scheme in transmitting/receiving at least part of the personal information.

8. A health management method of managing health of each patient carrying a portable terminal, including the steps of:

providing a portable terminal carried by a patient with a display screen, radio communication means for accessing a predetermined radio communication network, storage means for storing personal information of the patient, an input/output device for supporting health management for the patient, and emergency notification means for transmitting to the radio communication network a type of emergency notification specified by the patient from a plurality of types of emergency notifications, wherein the personal information includes information of a clinical chart of the patient and a prescription of the patient;

providing a database for communicating with each portable terminal with personal information storage means for storing the personal information about each patient carrying the portable terminal, medical information storage means for storing information about a medical facility, a drugstore, a medicine, and the input/output device, and communication means for communicating with the portable terminal through the radio communication network;

transmitting part of the personal information stored in the storage means by the radio communication means when starting to communicate with the database;

identifying, using the database, the patient of the portable terminal by collating the part of the information transmitted from the radio communication means with information stored in the personal information storage means; and activating, when the type of emergency notification is transmitted from said emergency notification means, an emergency handling means which provides, in accordance with the type of emergency notification, said portable terminal either with communication or with information, wherein the communication provided to said portable terminal uses said radio communication means to communicate with a medical facility whose information is stored in said medical information storage means, and wherein the information provided to the portable terminal comprises information about a medical facility or a drugstore providing a medicine needed for the identified patient, and wherein the information is selected from information stored in said medical information storage means based on at least one of the clinical chart and the prescription of the patient wherein the input/output device is an inhaler for discharging a medicine in the form of fine droplets to make the patient inhale the droplets, and the information about the input/output device includes information about handling of the inhaler, and said portable terminal further comprises position information acquisition means for acquiring position information of said terminal, and, in the step of activating, said emergency handling means causes said portable terminal to display information about a route from a position of said portable terminal to a suitable medical facility or drugstore on said display screen on the basis of the position information of transmitted from said position information acquisition means.

9. The method according to claim 6, wherein in the database, when no information is transmitted a predetermined period of time after a specific signal is transmitted from the radio communication means, communication is made to an emergency facility.

10. The method according to claim 6, wherein part of the information includes information about biometrical characteristics of the patient.

11. An information provision method for providing medical information about health, a medical treatment or a medicine from a database, comprising steps of:

receiving, from a portable terminal carried by a patient through a network, patient information stored in the portable terminal and a type of emergency notification specified by the patient from a plurality of types of emergency notifications, wherein the patient information includes a clinical chart of the patient and a prescription of the patient;

identifying the patient by collating the patient information transmitted from the portable terminal with personal information stored in the database; and activating an emergency handling means which is included in the database and which provides, in accordance with the type of emergency notification, said portable terminal either with communication or with information, wherein the communication provided to said portable terminal uses said radio communication means to communicate with a medical facility whose information is stored in said medical information storage means, and wherein the information provided to said portable terminal comprises information which is about a medical facility or a drugstore providing a medicine needed for the identified patient, and wherein the information is selected from information stored in said medical information storage means based on at least one of the clinical chart and the prescription of the patient, wherein said portable terminal further comprises position information acquisition means for acquiring position information of said terminal, and, in the step of activating, said emergency handling means causes said portable terminal to display information about a route from a position of said portable terminal to a suitable medical facility or drugstore on said display screen on the basis of the position information transmitted from said position information acquisition means.

12. An information provision method for providing medical information about health, a medical treatment or a medicine from a database, comprising steps of:

receiving, from a portable terminal carried by a patient through a network, patient information stored in the portable terminal and a type of emergency notification specified by the patient from a plurality of types of emergency notifications by the radio communication network;

identifying the patient by collating the patient information transmitted from the portable terminal with personal information stored in the database, wherein the personal information includes information of a clinical chart of the patient and a prescription of the patient; and activating an emergency handling means which is included in the database and which provides, in accordance with the type of emergency notification, said portable terminal either with communication or with information, wherein the communication provided to said portable terminal uses said portable terminal to communicate with a medical facility whose information is stored in said database, and wherein the information provided to said portable terminal comprises information about a medical facility or a drugstore providing a medicine needed for the identified patient, and wherein the information is selected from information stored in said database based on at least one of the clinical chart and the prescription of the patient, wherein said portable terminal includes an inhaler which discharges a medicine on the basis of an ink-jet scheme using heat, and said portable terminal further comprises position information acquisition means for acquiring position information of said terminal, and, in the step of activating, said emergency handling means causes said portable terminal to display information about a route from a position of said portable terminal to a suitable medical facility or drugstore on said display screen on the basis of the position information transmitted from said position information acquisition means.

13. The method according to claim 11, wherein the medical information is route information about a suitable medical facility or drugstore for the identified patient.

14. A health management system for managing health of each user carrying a portable terminal, comprising:

a portable terminal which is arranged to be carried by a user and includes a display screen, radio communication means for accessing a predetermined radio communication network, storage means for storing personal information of the user, wherein the personal information includes information of a clinical chart of the user and a prescription of the user, an input/output device including a medication device for supporting health management for the user, and emergency notification means for transmitting to the radio communication network a type of emergency notification specified by the user from a plurality of types of emergency notifications; and a database including personal information storage means for storing the personal information about each user carrying said portable terminal, medical information storage means for storing information about a medical facility, a drugstore, a medicine, and said input/output device; and communication means for communicating with said portable terminal through the radio communication network, wherein said radio communication means transmits part of the personal information stored in said storage means in starting to communicate with said database, and wherein said database further includes identification means for identifying the user of said portable terminal by collating the part of the information transmitted from said radio communication means with information stored in said personal information storage means, and emergency handling means which is activated when the type of emergency notification is transmitted from said emergency notification means and which provides, in accordance with the type of emergency notification, said portable terminal either with communication or with information, wherein the communication provided to said portable terminal uses said radio communication means to communicate with a medical facility whose information is stored in said medical information storage means, and wherein the information provided to said portable terminal comprises information which is about a medical facility or a drugstore providing a medicine needed for the identified user, and wherein the information is selected from information stored in said medical information storage means based on at least one of the clinical chart and the prescription of the user.

15. The system according to claim 14, wherein said radio communication means and said communication means perform encryption/decryption in transmitting/receiving at least part of the personal information.

16. The system according to claim 14, wherein said portable terminal further comprises position information acquisition means for acquiring position information of said portable terminal, and displaying information about a route to the medical facility or the drugstore selected by said emergency handling means on said display screen based on the position information.

17. The system according to claim 14, wherein said medication device is an inhaler for discharging a medicine in the form of fine droplets to make the user inhale the droplets, and the information about said input/output device includes information about handling of said inhaler.

18. The system according to claim 14, wherein said emergency handing means communicates with an emergency facility when no information is transmitted for a predetermined period of time after said emergency handling means is activated.

19. The system according to claim 14, wherein part of the information includes information about biometrical characteristics of the user.

20. A health management method of managing health of each user carrying a portable terminal, including the steps of:
providing a portable terminal carried by a user with a display screen, radio communication means for accessing a predetermined radio communication network, storage means for storing personal information of the user including information of a clinical chart of the user and a prescription of the user, an input/output device including a medication device for supporting health management for the user, and emergency notification means for transmitting to the radio communication network a type of emergency notification specified by the user from a plurality of types of emergency notifications;
providing a database for communicating with each portable terminal with personal information storage means for storing the personal information about each user carrying the portable terminal, medical information storage means for storing information about a medical facility, a drugstore, a medicine, and the input/output device, and communication means for communicating with the portable terminal through the radio communication network;
transmitting part of the personal information stored in the storage means by the radio communication means when starting to communicate with the database;
identifying using the database, the user of the portable terminal by collating the part of the information transmitted from the radio communication means with information stored in the personal information storage means; and
activating an emergency handling means when the type of emergency notification is transmitted from said emergency notification means, wherein the emergency handling means provides, in accordance with the type of emergency notification, said portable terminal either with communication or with information, wherein the communication provided to said portable terminal uses said radio communication means to communicate with a medical facility whose information is stored in said medical information storage means, and wherein the information provided to said portable terminal comprises information about a medical facility or a drugstore providing a medicine needed for the identified user, and wherein the information is selected from information stored in said medical information storage means based on at least one of the clinical chart and the prescription of the user.

21. The method according to claim 20, wherein said radio communication means and said communication means perform encryption/decryption in transmitting/receiving at least part of the personal information.

22. The method according to claim 20, further including the steps of:
acquiring position information of said portable terminal using position information acquisition means, and
displaying information about a route to the medical facility or the drugstore selected from the database on said display screen based on the position information.

23. The method according to claim 20, wherein said medication device is an inhaler for discharging a medicine in the form of fine droplets to make the user inhale the droplets, and the information about said input/output device includes information about handling of said inhaler.

24. The method according to claim 20, further including the step of communicating with an emergency facility in the database when no information is transmitted for a predetermined period of time after said emergency handling means is activated.

25. The method according to claim 20, wherein part of the information includes information about biometrical characteristics of the user.

26. A health management system for providing medical information about health, a medical treatment or a medicine from a database, comprising:
means for receiving, from a portable terminal including a medication device via a network, information including a clinical chart of a user and a prescription of the user stored in the portable terminal, and a type of emergency notification specified by the user from a plurality of types of emergency notifications;
identification means for identifying the user of said portable terminal by collating the received information with personal information stored in said database, and
means for conducting the identification in response to transmission of the type of emergency notification from said portable terminal, and for providing, in accordance with the type of emergency notification, said portable terminal either with communication or with information, wherein the communication provided to said portable terminal uses said portable terminal to communicate with a medical facility whose information is stored in said database, and wherein the information provided to the portable terminal comprises information about a medical facility or a drugstore providing a medicine needed for the identified user, and wherein the information is selected from information stored in said database.

27. The system according to claim 26, wherein said medication device includes an inhaler discharging a medicine on the basis of the ink-jet scheme using heat.

* * * * *